(12) United States Patent
Tam et al.

(10) Patent No.: US 6,261,320 B1
(45) Date of Patent: Jul. 17, 2001

(54) RADIOACTIVE VASCULAR LINER

(75) Inventors: Lisa A. Tam, Lake Forest; Brett A. Trauthen, Newport Beach, both of CA (US)

(73) Assignee: Radiance Medical Systems, Inc., Irvine, CA (US)

( * ) Notice: Subject to any disclaimer, the term of this patent is extended or adjusted under 35 U.S.C. 154(b) by 0 days.

(21) Appl. No.: 09/253,177

(22) Filed: Feb. 19, 1999

Related U.S. Application Data

(63) Continuation-in-part of application No. 08/975,584, filed on Nov. 21, 1997, now Pat. No. 6,120,535, which is a continuation-in-part of application No. 08/881,956, filed on Jun. 25, 1997, now Pat. No. 6,090,136, which is a continuation-in-part of application No. 08/754,816, filed on Nov. 21, 1996, now Pat. No. 5,728,150.

(51) Int. Cl.<sup>7</sup> ....................................... A61F 2/00

(52) U.S. Cl. ..................... 623/1.15; 623/1.4; 623/1.39
(58) Field of Search ....................... 623/1.15, 1.2, 623/1.36, 1.39, 1.4

(56) References Cited

U.S. PATENT DOCUMENTS

| Re. 34,327 | 7/1993 | Kreamer . |
|---|---|---|
| 3,324,847 | 6/1967 | Zoumboulis . |
| 4,115,536 | 9/1978 | Rothman et al. . |
| 4,124,705 | 11/1978 | Rothman et al. . |
| 4,126,669 | 11/1978 | Rothman et al. . |
| 4,225,790 | 9/1980 | Parsons, Jr. et al. . |
| 4,323,055 | 4/1982 | Kubiatowicz . |
| 4,423,725 | 1/1984 | Baran et al. . |
| 4,581,017 | 4/1986 | Sahota . |
| 4,588,395 | 5/1986 | Lemelson . |
| 4,655,771 | 4/1987 | Wallsten . |
| 4,665,918 | 5/1987 | Garza et al. . |
| 4,674,480 | 6/1987 | Lemelson . |
| 4,706,652 | 11/1987 | Horowitz . |
| 4,739,762 | 4/1988 | Palmaz . |
| 4,740,207 | 4/1988 | Kreamer . |
| 4,762,129 | 8/1988 | Bonzel . |
| 4,776,337 | 10/1988 | Palmaz . |
| 4,800,882 | 1/1989 | Gianturco . |
| 4,815,449 | 3/1989 | Horowitz . |
| 4,819,618 | 4/1989 | Liprie . |
| 4,877,030 | 10/1989 | Beck et al. . |
| 4,878,492 | 11/1989 | Sinofsky et al. . |
| 4,922,905 | 5/1990 | Strecker . |
| 5,007,926 | 4/1991 | Derbyhire . |
| 5,011,677 | 4/1991 | Day et al. . |
| 5,019,369 | 5/1991 | Presant et al. . |
| 5,040,548 | 8/1991 | Yock . |
| 5,059,166 | 10/1991 | Fischell et al. . |
| 5,059,211 | 10/1991 | Stack et al. . |

(List continued on next page.)

FOREIGN PATENT DOCUMENTS

| 0 433 011 B1 | 7/1994 | (EP) . |
|---|---|---|
| 0 688 580 A1 | 12/1995 | (EP) . |
| 0 593 136 B1 | 3/1997 | (EP) . |

(List continued on next page.)

OTHER PUBLICATIONS

Radiation Quantities and Units, ICRU Report 33, International Commisson on Radiation, Units and Measurements, Apr. 15, 1980.

(List continued on next page.)

*Primary Examiner*—Michael J. Milano
(74) *Attorney, Agent, or Firm*—Knobbe, Martens, Olson & Bear LLP

(57) ABSTRACT

Disclosed is a radioactive tubular prosthesis formed by rolling a flexible sheet around a longitudinal axis. Preferably, the prosthesis is self expandable under the radially outwardly directed spring bias of the rolled sheet. At least a portion of the sheet is provided with a coating comprising at least one radioisotope.

11 Claims, 10 Drawing Sheets

U.S. PATENT DOCUMENTS

| | | |
|---|---|---|
| 5,061,273 | 10/1991 | Yock . |
| 5,078,726 | 1/1992 | Kreamer . |
| 5,089,006 | 2/1992 | Stiles . |
| 5,100,429 | 3/1992 | Sinofsky et al. . |
| 5,106,360 | 4/1992 | Ishiwara et al. . |
| 5,167,614 | 12/1992 | Tessmann et al. . |
| 5,171,262 | 12/1992 | MacGregor . |
| 5,176,617 | 1/1993 | Fischell et al. . |
| 5,192,307 | 3/1993 | Wall . |
| 5,199,939 | 4/1993 | Dake et al. . |
| 5,213,561 | 5/1993 | Weinstein et al. . |
| 5,234,448 | 8/1993 | Wholey et al. . |
| 5,242,399 | 9/1993 | Lau et al. . |
| 5,254,127 | 10/1993 | Wholey et al. . |
| 5,266,073 | 11/1993 | Wall . |
| 5,267,960 | 12/1993 | Hayman et al. . |
| 5,302,168 | 4/1994 | Hess . |
| 5,302,369 | 4/1994 | Day et al. . |
| 5,306,286 | 4/1994 | Stack et al. . |
| 5,306,294 | 4/1994 | Winston et al. . |
| 5,344,426 | 9/1994 | Lau et al. . |
| 5,354,257 | 10/1994 | Roubin et al. . |
| 5,354,309 | 10/1994 | Schnepp-Pesch et al. . |
| 5,366,473 | 11/1994 | Winston et al. . |
| 5,383,926 | 1/1995 | Lock et al. . |
| 5,405,379 | 4/1995 | Lane . |
| 5,411,466 | 5/1995 | Hess . |
| 5,411,549 | 5/1995 | Peters . |
| 5,411,551 | 5/1995 | Winston et al. . |
| 5,423,885 | 6/1995 | Williams . |
| 5,424,288 | 6/1995 | Order . |
| 5,441,515 | 8/1995 | Khosravi et al. . |
| 5,443,500 | 8/1995 | Sigwart . |
| 5,449,382 | 9/1995 | Dayton . |
| 5,484,384 | 1/1996 | Fearnot . |
| 5,498,227 | 3/1996 | Mawad . |
| 5,503,613 | 4/1996 | Weinberger . |
| 5,540,659 | 7/1996 | Tierstein . |
| 5,540,713 | 7/1996 | Schnepp-Pesch et al. . |
| 5,605,530 | 2/1997 | Fischell et al. . |
| 5,616,114 | 4/1997 | Thornton et al. . |
| 5,618,266 | 4/1997 | Liprie . |
| 5,643,171 | 7/1997 | Bradshaw et al. . |
| 5,653,683 | 8/1997 | D'Andrea . |
| 5,662,580 | 9/1997 | Bradshaw et al. . |
| 5,674,177 | 10/1997 | Hehrlein et al. . |
| 5,683,345 | 11/1997 | Waksman et al. . |
| 5,688,220 | 11/1997 | Verin et al. . |
| 5,707,332 | 1/1998 | Weinberger . |
| 5,713,828 | 2/1998 | Coniglione . |
| 5,720,717 | 2/1998 | D'Andera . |
| 5,722,984 | 3/1998 | Fischell et al. . |
| 5,723,003 | 3/1998 | Winston et al. . |
| 5,728,042 | 3/1998 | Schwager . |
| 5,728,150 | 3/1998 | McDonald et al. . |
| 5,730,698 | 3/1998 | Fischell et al. . |
| 5,755,690 | 5/1998 | Saab . |
| 5,762,631 | 6/1998 | Klein . |
| 5,782,740 | 7/1998 | Schneiderman . |
| 5,782,741 | 7/1998 | Bradshaw et al. . |
| 5,782,742 | 7/1998 | Crocker et al. . |
| 5,795,286 | 8/1998 | Fischell et al. . |
| 5,860,991 | 1/1999 | Klein et al. . |
| 5,863,284 | 1/1999 | Klein . |
| 5,871,436 | 2/1999 | Eury . |
| 5,879,282 | 3/1999 | Fischell et al. . |
| 6,013,019 | 1/2000 | Fischell et al. . |
| 6,019,718 | 2/2000 | Hektner . |
| 6,024,690 | 2/2000 | Lee et al. . |
| 6,033,357 | 3/2000 | Ciezki et al. . |
| 6,042,600 | 3/2000 | Rosenthal et al. . |
| 6,050,930 | 4/2000 | Teirstein . |
| 6,059,713 | 5/2000 | Urick et al. . |
| 6,059,714 | 5/2000 | Armini et al. . |
| 6,059,752 | 5/2000 | Segal . |

FOREIGN PATENT DOCUMENTS

| | | |
|---|---|---|
| WO 93/04735 | 3/1993 | (WO) . |
| WO 94/23789 | 10/1994 | (WO) . |
| WO 94/26205 | 11/1994 | (WO) . |
| WO 95/19807 | 7/1995 | (WO) . |
| WO 95/29008 | 11/1995 | (WO) . |
| WO 96/10436 | 4/1996 | (WO) . |
| WO 96/13303 | 5/1996 | (WO) . |
| WO 96/14898 | 5/1996 | (WO) . |
| WO 96/22121 | 7/1996 | (WO) . |
| WO 97/18012 | 5/1997 | (WO) . |

OTHER PUBLICATIONS

Scanning Electron Microscopy Evaluation of Porous and Nonporous Arterial Substitutes, Giovanni B. Ratto, M.D., Carmen Lunghi, M.D., Enzo Spinelli, M.D., Riccardo Agati, M.D., Marzia Tomellini, M.D., and Giovanni Motta, M.D., Genoa, Italy, Surgery, Gynecology & Obstetrics, Sep. 1982, vol. 155.

Morphology of Healing in Vascular Prosthesis, G. Rahlf, P. Urban, and R.M. Bohle, Read at the 14th Annual Meeting of the German Society for Thoracic and Cardiovascular Surgery, Bad Nauheim 1985, Thoracic Cardiovascular Surgeon 34 (1986).

Endothelial Cell Adhesion to Vascular Prosthetic Surfaces, D. Gourevitch, Carolyn E. Jones, J. Crocker and M. Goldman, Presented at Biointeractions '87, Cambridge, UK in Jul. 1987, Biomaterials 1988, vol. 9, Jan.

Restenosis After Ballon Angioplasty, A Practical Proliferative Model in Porcine Coronary Arteries, Robert S. Schwartz, MD, Joseph G. Murphy, MB, William D. Edwards, MD. Allan R. Camrud, RN, Ronald E. Vlietstra, MB, BCh, and David R. Holmes, MD, Circulation, vol. 82, No. 6, Dec. 1990.

Effects of high–dose intracoronary irradiation on vasomotor function and smooth muscle histopathology, Joseph G. Wiederman, Jeffery A. Leavy, Howard Armols, Allan Schwartz, Shunichi Homma, Charles Marboe and Judah Weinberger, Interventional Cardiology Center, Department of Medicine and Radiation Oncology and Section of Cardiac Pathology, Columbia–Presbyterian Medical Center and Columbia University, 1994 the American Physiological Society.

Intracoronary Irratiation Markedly Reduces Restenosis Restenosis After Ballon Angioplasty in a Procine Model, Joseph G. Wiedermann, MD, Charles Marboe, MD, Howard Amols, PhD, Allan Schwartz, MD, FACC, Judah Weinberger, MD, PhD, FACC, JACC, vol. 23. No. 6, May 1994:1491–8.

Intracoronary Irradiation Markedly Reduces Neointimal Proliferation After Balloon Angioplasty in a Swine: Persistant Benefit at 6–Month Follow–up, Joseph G. Wiedermann, MD, Charles Marboe, MD, Howard Amols, PhD, Allan Schwartz, MD, FACC, Judah Weinberger, MD, PhD, FACC, JACC, vol. 25. No. 6, May 1995:1451–6.

Discoveries in Radiation for Restenosis, Emory University of School of Medicine, Presented by The Andreas Gruentzig Cardiovascular Center and the Department of Radiation Oncology of Emory University School of Medicine; J.W. Marriott Hotel at Lenox, Atlanta, GA, Jan. 11–12, 1996.

Radioactive Balloon Catheter to Inhibit Restenosis after Angioplasty.

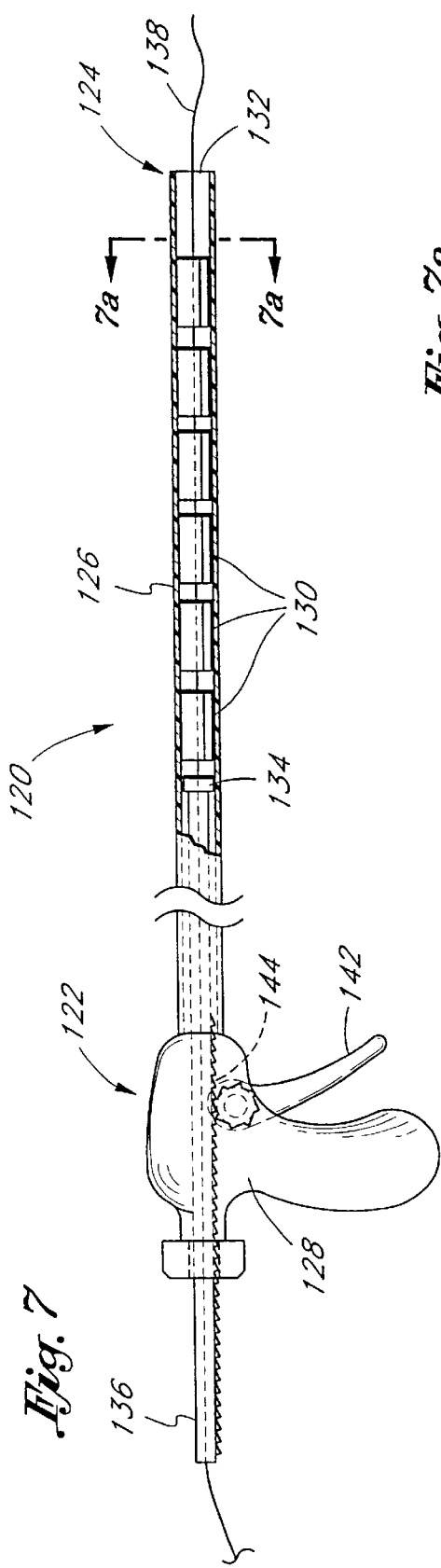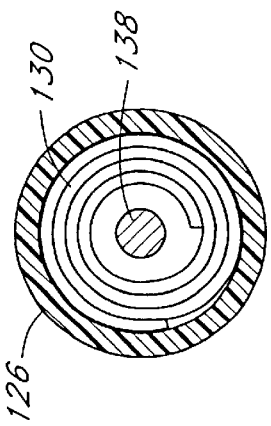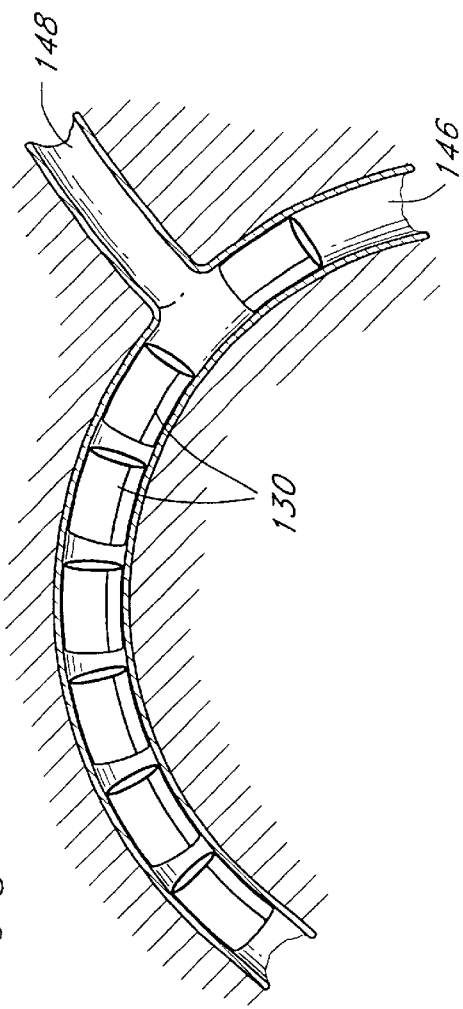

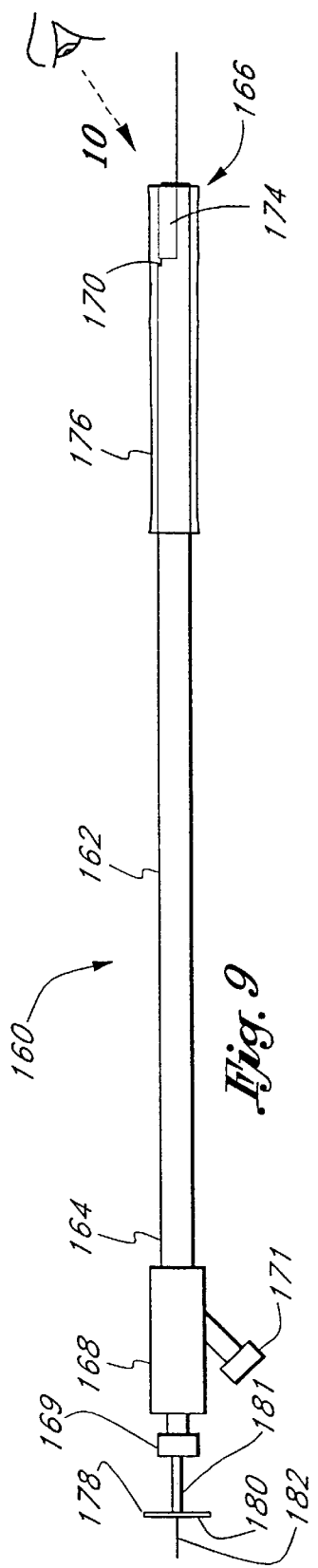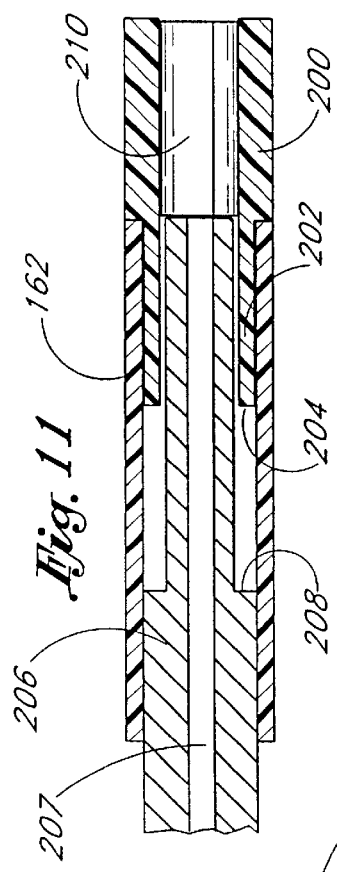

RADIOACTIVE VASCULAR LINER

CROSS-REFERENCE TO RELATED APPLICATION

This is a continuation-in-part of commonly assigned, U.S. patent application Ser. No. 08/975,584 filed Nov. 21, 1997, now U.S. Pat. No. 6,120,535, which is a continuation-in-part of U.S. patent application Ser. No. 08/881,956 filed Jun. 25, 1997, now U.S. Pat. No. 6,090,136, which is a continuation-in-part of U.S. patent application Ser. No. 08/754,816 filed Nov. 21, 1996, now U.S. Pat. No. 5,728,150.

FIELD OF THE INVENTION

The present invention relates to coated or covered intraluminal stents and grafts that are adapted to be advanced in a collapsed roll to the site of an aneurysm, defect or injury of a body vessel and expanded or allowed to self expand across the site, wherein said coating or covering comprises at least one radioisotope.

BACKGROUND OF THE INVENTION

PTA treatment of the coronary arteries, percutaneous transluminal coronary angioplasty (PTCA), also known as balloon angioplasty, is the predominant treatment for coronary vessel stenosis. Approximately 300,000 procedures were performed in the United States in 1990 and nearly one million procedures worldwide in 1997. The U.S. market constitutes roughly half of the total market for this procedure. The increasing popularity of the PTCA procedure is attributable to its relatively high success rate, and its minimal invasiveness compared with coronary by-pass surgery. Patients treated by PTCA, however, suffer from a high incidence of restenosis, with about 35% or more of all patients requiring repeat PTCA procedures or by-pass surgery, with attendant high cost and added patient risk.

More recent attempts to prevent restenosis by use of drugs, mechanical devices, and other experimental procedures have had limited long term success. Stents, for example, dramatically reduce acute reclosure, and slow the clinical effects of smooth muscle cell proliferation by enlarging the minimum luminal diameter, but otherwise do nothing to prevent the proliferative response to the angioplasty induced injury.

Restenosis is now believed to occur at least in part as a result of injury to the arterial wall during the lumen opening angioplasty procedure. In some patients, the injury initiates a repair response that is characterized by hyperplastic growth of the vascular smooth muscle cells in the region traumatized by the angioplasty. Intimal hyperplasia or smooth muscle cell proliferation narrows the lumen that was opened by the angioplasty, regardless of the presence of a stent, thereby necessitating a repeat PTCA or other procedure to alleviate the restenosis.

Preliminary studies indicate that intravascular radiotherapy (IVRT) has promise in the prevention or long-term control of restenosis following angioplasty. IVRT may also be used to prevent or delay stenosis following cardiovascular graft procedures or other trauma to the vessel wall. Proper control of the radiation dosage, however, appears to be important to inhibit or arrest hyperplasia without causing excessive damage to healthy tissue. Overdosing of a section of blood vessel can cause arterial necrosis, inflammation, hemorrhaging, and other risks discussed below. Underdosing will result in inadequate inhibition of smooth muscle cell hyperplasia, or even exacerbation of hyperplasia and resulting restenosis.

U.S. Pat. No. 5,059,166 to Fischell discloses an IVRT method that relies on a radioactive stent that is permanently implanted in the blood vessel after completion of the lumen opening procedure. Radiation delivery systems provided on a stent have also been disclosed in U.S. Pat. No. 5,176,617 to Fischell et al., and in U.S. Pat. No. 5,674,177 to Heirlein et al. The use of a stent as a platform is of particular interest because it has been shown to be effective in animals, even at activity ranges as low as 0.14–0.23 $\mu$Ci (microcuries). Refer, for example, to Fischell, et al., ALow-Dose, β-Particle Emission From Stent Wire Results in Complete, Localized Inhibition of Smooth Muscle Cell Proliferation", *Circulation*, vol. 90, pp. 2956–2963, (1994); Laird et al, AInhibition of Neointimal Proliferation with Low-Dose Irradiation From a β-Particle-Emitting Stent", *Circulation*, 93:529–536 (1996); Carter, et al, AEffects of Endovascular Radiation From a β-Particle Emitting Stent in a Porcine Coronary Restenosis Model [A Dose-Response Study]@, *Circulation* 92:1570–1575 (1995); and Hehrlein, et al, APure β-Particle-Emitting Stents Inhibit Neointima Formation in Rabbits", *Circulation* 93:641–645 (1996).

Several limitations exist in the systems disclosed in the literature and in the currently available art. One limitation is that the isotope chosen for the radiation is dependent on the materials used for the stent. For example, in the systems described in Fischell '617 and '166, Hehrlein '177, and in the stents used in the experiments described by Fischell and Hehrlein in their 1995 papers cited above, the active isotopes were limited to species created by direct neutron activation of the stent in a reactor. This process limits control over the type and amount of radiation that the stent can possess. Hehrlein '177 discloses no less than nine different isotopes created by this process, each with its own half-life, activity level, and radiation characteristics. This set up makes control over the radiation dose extremely difficult, and investigation into the interaction of the radiation with tissue very problematic.

To overcome this limitation, the stents used in the study described by Laird were made by first ion implanting the stent with phosphorous-31 (P-31 or $^{31}$P), then placing the stents in a reactor to convert the stable P-31 to the beta-emitting P-32. Alternatively, the radioactive stent described in Fischell '166 and '617 describe coating or otherwise encapsulating a cold version of the target isotope in the stent material, and then placing the stent in a reactor to convert the stable isotope to a radioactive one. This approach, while offering some improvement over the prior method, is limited in the total activity attainable. For example, consider the activation of P-32 by neutron bombardment. Only about 1 in every 100,000 P-31 ions is converted to P-32 in the reactor chamber over a 10-day period. While this conversion rate can be increased, there is a physical limitation to this process dictated by the reactor flux, the cross section of the target atom, and the half-life of the isotope. Moreover, this method does not completely eliminate the activation of non-desired isotopes created from the stent material.

A second limitation relates to the geometry of the prior art radioactive stents. In general, balloon expandable stents comprise a plurality of struts which are spaced apart from each other when the stent is in the expanded state. A radioactive coating or ion implantation into such stents produces a radiation grid pattern which inherently delivers a nonuniform dose of radiation to the vessel wall. Many self expanding stent configurations also produce a nonuniform delivery profile.

Thus, there remains a need for a radioactive vascular liner such as a stent which is capable of delivering a substantially uniform dose of radiation throughout its delivery zone.

SUMMARY OF THE INVENTION

There is provided in accordance with one aspect of the present invention, a tubular vascular liner for delivering a dose of radiation to the wall of a vessel. The liner comprises a flexible sheet, rolled into a tube having a first diameter for positioning at a site in a vessel. The sheet is unrollable to second, larger diameter for positioning against the wall of the vessel. A radioactive isotope is attached to the sheet, such that the radioisotope is positioned adjacent the vessel wall when the sheet is implanted and enlarged to the second diameter.

Preferably, the sheet is self expandable from the first diameter to the second diameter. In one embodiment, an outer protective coating is provided to minimize the escape of radioisotope from the sheet.

In accordance with another aspect of the present invention, there is provided a radioactive tubular prosthesis. The prosthesis comprises a flexible sheet having a first edge and a second edge. The sheet is rollable into a tube such that the first edge is disposed on the inside of the tube and the second edge is disposed on the outside of the tube. A first transition zone is provided near the first edge, and a second transition zone is provided near the second edge. The first transition zone has an increasing flexibility in the direction of the first edge, and the second transition zone has an increasing flexibility in the direction of the second edge. At least a portion of the sheet is provided with a radioactive coating.

In accordance with another aspect of the present invention there is provided a self expandable radioactive tubular prosthesis. The prosthesis comprises a flexible perforated sheet rolled a first number of revolutions about an axis into a first, insertion diameter. The prosthesis is radially expandable under its own bias by unrolling to a substantially cylindrical prosthesis having a second, implanted diameter with a second, smaller number of revolutions. A sufficient number of perforations through adjacent layers of the sheet align to produce a plurality of ports extending all the way through the side wall of the prosthesis. Preferably, the sheet is provided with zones of differing spring strengths so that an innermost revolution of the sheet conforms substantially to the wall of the cylinder. At least a portion of the sheet is provided with a radioactive coating.

In accordance with a further aspect of the present invention, there is provided a tubular radioactive prosthesis. The prosthesis comprises a flexible sheet, having a longitudinal axis and at least first, second and third groups of apertures extending therethrough. The first group of apertures comprises a first plurality of parallel slots inclined at a first angle with respect to the longitudinal axis. The second group comprises a second plurality of parallel slots inclined at a second angle with respect to the longitudinal axis. The first, second and third groups of apertures are arranged on the sheet such that when the sheet is wrapped about an axis through at least about three revolutions to form a tubular prosthesis, at least some apertures from the first, second and third groups align to produce a plurality of ports extending through the side wall of the prosthesis. A radioactive coating is provided on at least a portion of the sheet.

These and other advantages and features of the invention will become apparent from the following detailed description of the preferred embodiments of the invention.

BRIEF DESCRIPTION OF THE DRAWINGS

FIG. 7 is a side elevational schematic illustration of a multiple vascular liner deployment tool in accordance with another aspect of the present invention.

FIG. 7a is a cross-sectional view through the line 7a—7a in FIG. 7.

FIG. 8 is a schematic view of a plurality of vascular liners of the present invention implanted within a curved vessel.

FIG. 9 is a side elevational schematic view of a vascular liner graft deployment tool in accordance with another aspect of the present invention.

FIG. 10 is a perspective view of a distal portion of the deployment tool of FIG. 9.

FIG. 11 is a cross-sectional view through the distal end of an alternate vascular liner graft deployment tool.

Figure 1:
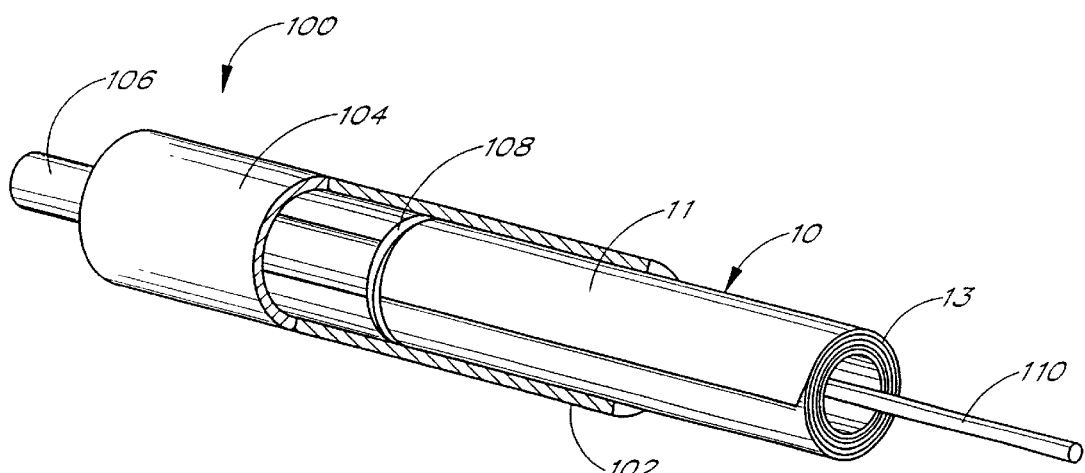
FIG. 1 is a fragmentary perspective view of a vascular liner in accordance with the present invention and the distal end of one exemplary form of a placement system for placing the vascular liner in its collapsed roll state at a desired site in a body lumen.

The drawing figures are not necessarily to scale.

DETAILED DESCRIPTION OF PREFERRED EMBODIMENTS

The present invention is described in the context of a vascular liner such as a tubular graft for intraluminally bridging an aneurysm, defect or injury, or a stent for supporting and maintaining a vessel lumen following an angioplasty or other procedure for opening the lumen. It will be understood that the invention may be incorporated into prostheses of all types for maintaining patency or for contacting the walls of lumens of blood vessels or other body ducts, hollow organs or vessels and that the expression "body lumen" includes all such lumens.

Turning to FIG. 1, it depicts a prosthesis 10 constructed in accordance with an embodiment of the invention in relation to an exemplary stent placement system 100 that may be used to intraluminally introduce and release the stent 10 at a desired body site. Alternate deployment systems and useful deployment methods are disclosed in U.S. Pat. Nos. 5,405,379, 5,306,294 and 5,336,473, the disclosures of which are incorporated herein by reference.

The stent 10 is shown in its retracted state and partially deployed from the distal end 102 of a tubular introducer catheter 104. The illustrated introducer catheter 104 has an inside diameter substantially equal to the outer diameter of the stent 10 when in its collapsed roll state. The catheter 104 is provided with at least one elongate lumen extending axially therethrough, for removably receiving a central core or pusher 106. In the illustrated embodiment, pusher 106 comprises an elongate flexible tubular element having an outside diameter which is less than the inside diameter of the catheter 104. The pusher 106 is therefore preferably provided with a stop 108 on the distal end thereof for permitting the pusher 106 to efficiently push at least one prosthesis 10 distally from the catheter 104. In use, the pusher 106 will generally be held in an axially fixed position and the catheter proximally withdrawn to deploy the prosthesis 10, as will be discussed below. Preferably, the catheter 104 is adapted to be introduced over a guidewire 110, which is axially slidably received through the coiled prosthesis 10 and through the lumen within pusher element 106.

As shown in FIG. 1, the prosthesis or stent 10 is formed of a sheet 11 that is rolled up into a tubular body 13 of a single layer or multiple overlapping layers of sheet 11. The tubular body 13 therefore has a side wall formed of the rolled up sheet 11, an inner lumen around the guide wire 110, and an axial length extending, in the longitudinal direction of the introducer catheter 104 between proximal and distal tubular body ends. The proximal tubular body end butts against the stop 108, and the distal tubular body end will generally be positioned near the distal end 102 of catheter 104. The guide wire 110 guides introduction of the distal end 102 of the outer introducer catheter 104 including the stent 10 within it to a body lumen site for deployment of the stent 10 in a manner generally taught in the above-referenced '294 and '473 patents, incorporated herein by reference in their entireties.

The reduced implantation diameter of the tubular body 13 is dictated by the inside diameter of the catheter 104. In an alternative embodiment of the placement system 100 such as that disclosed in the '294 patent, the outer sheath 104 is not used and cords (not shown in FIG. 1) are used to restrain the sheet 11 in the collapsed roll state until the cords are withdrawn all in a manner taught in the above-incorporated '294 patents.

In accordance with a method of installation using the depicted placement system 100, the perforated sheet 11 is rolled up into a tubular stent 13 such as by rolling the sheet 11 around a mandril (not illustrated). The rolled tubular body 13 is then loaded into the distal end 102 of the introduction catheter 104, either at a point of manufacture, or at the clinical site. The radially outwardly directed bias of the tubular body 13, as discussed in greater detail infra, causes the tubular body 13 to press radially outwardly against the interior wall of the catheter 104, thereby retaining the tubular body 13 in position within the catheter 104. The introducer catheter 104 and the stent 10 are thereafter introduced over the guide wire 110 and advanced transluminally to the desired body lumen site with the tubular body 13 restrained in the collapsed roll state. At the site, the pusher 106 is advanced distally with respect to the catheter 104 to expel the stent 10 out of the distal end opening of catheter 104. Preferably, the catheter 104 is withdrawn proximally while the pusher 106 is maintained stationary in the vessel. The released tubular body 13 self expands in diameter to its expanded roll state constrained in size by the diameter of the body lumen at the site.

The placement system 100 of FIG. 1 and the method of placement described above provide one example of a system and method for collapsing the stent 10 and for effecting its introduction and release at the site that may be employed with the improved stent 10 of the present invention. Any of a variety of alternate deployment systems can also be used as will be apparent to persons of skill in the art in view of the disclosure herein.

Moreover, the perforation pattern of the stent sheet of the present invention may be incorporated into stents that are not self expanding and are expanded at the site by expansion mechanisms. In such a case, the stent expanded roll state would still have multiple layers of the sheet in the side wall thereof as shown in the remaining figures.

Returning to FIGS. 1–3, the tubular body 13 is formed of a sheet 11 of biocompatible material rolled into a plurality of layers to form the side wall and a central lumen. The tubular body 13 therefore presents a plurality of adjacent arcuate layers of the sheet 11 rolled up in a direction transverse to the longitudinal direction and the longitudinal axis of the stent 10. The sheet 11 possesses an inherent resilience and spring force that seeks to unwind the wound layers and expand the stent lumen as described in the above-incorporated '294 patent, for example. In the fully expanded roll state within a vessel, there are at least about 1½ to 4 or more fully overlapping layers that bear against one another under the spring force, when the prosthesis is intended to resist collapse. In an embodiment intended to deliver radiation but not also function as a mechanical support, a single complete circumference with no or minimal overlap may be sufficient.

In general, the optimum number of overlapping layers or fractional layers in the implanted, expanded configuration will depend upon a variety of factors as is discussed elsewhere herein. For example, sufficient overlapping surface area to resist collapse under radially inwardly directed pressure from the artery is desirable. Factors such as sheet thickness, spring force, and effects of various coatings upon the coefficient of static friction may affect the minimum area of overlap necessary to resist collapse. Although excessive overlapping layers (e.g. 3 or 4 or 5 or more) provide increased radial strength, they may prohibit the use of a balloon to post dilate or size the stent following initial deployment. For applications in which post deployment dilatation is desired, a relatively fewer layers are preferred. Thus, overlap on the order of ½ layer or one full layer or 1½ layer or 2 layers or even 2½ layers may be desirable for stents intended for post deployment dilation. Additional considerations which affect the optimum overlap are disclosed elsewhere herein. In general, for any intended implanted diameter, sheet thickness, and surface material, the optimum number of overlaps for a target artery size can be readily determined through routine experimentation by those of skill in the art in view of the disclosure herein.

Figure 2:
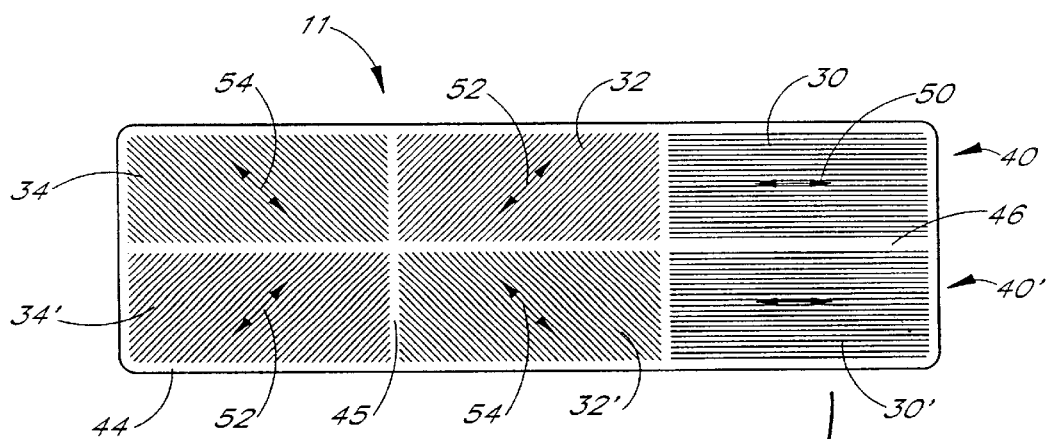
FIG. 2 is a plan view of one sheet pattern from which the vascular liner of the present invention is formed showing the symmetrical orientation of a pair of first, second and third zones of the sheet containing elongated perforations orientated at complementary angles to one another.
Figure 3:
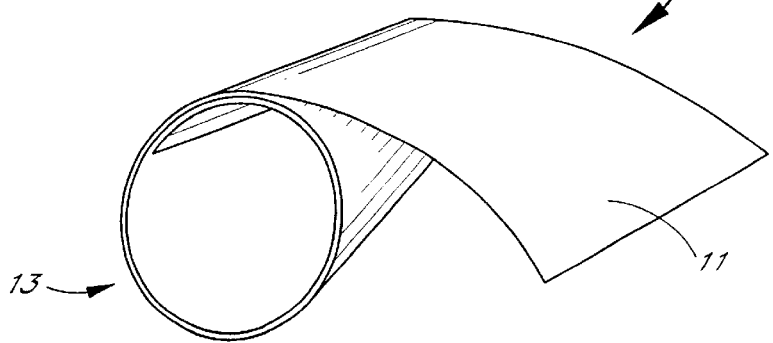
FIG. 3 is a schematic illustration of the sheet of FIG. 2 being rolled into a tubular prosthesis.

Turning to FIG. 2, the sheet 11 is shown flattened out to illustrate the perforation pattern employed in a preferred embodiment of the present invention to assure that openings extend through the multiple layers of the rolled up sheet 11 forming the tubular body 13 in the expanded roll state. The sheet 11 has a sheet length SL providing the plurality of overlapping layers when the sheet 11 is rolled up in the length direction and a sheet width SW corresponding to the axial length of tubular body 13. The sheet width SW and length SL in one 3 cm embodiment are on the order of about 30.0 mm and 116.0 mm, respectively, resulting in a tubular body length of about 30 mm. The sheet 11 may be formed of a biocompatible metal alloy, e.g., Elgiloy, in a foil of a thickness of about 0.0015 inches (about 0.038 mm).

It is contemplated that a sheet 11 having an SL of 116 mm and thickness of about 0.0015 inches may be wound into a collapsed roll state to fit within an introducer sheath lumen of about 3.9 mm in inside diameter and have an inner diameter of about 1.3 mm, in which the number of layers in the tubular member side wall approaches 18. When released in situ, the outer diameter of the tubular member 13 may expand to between 12 mm and 18 mm, resulting in between 3 and 2 layers, respectively, forming the side wall of tubular member 13.

In general, the length of the tubular body 13 (which will normally equal the sheet width of the sheet 11) is selected to optimize performance of the prosthesis in the intended use environment. For example, in an application where the prosthesis is intended to be used as a graft for treating a tubular abdominal aortic aneurysm, the sheet width will generally be within the range of from about 75 mm to about 200 mm. Preferably, the sheet width is selected to provide a graft having an axial length which is greater than the length of the aneurysm or other diseased site being treated. Preferably, each of the proximal and distal ends of the graft will overlap with healthy vessel for a distance of at least about 10 mm. A relatively greater overlap, such as on the order of 15 mm or greater, may be desirable in straight sections of the aorta, to optimize anchoring and tacking down of the ends of the graft by way of neointimal growth.

The illustrated sheet 11 is provided with a plurality of perforation zones 30, 32, 34 and 30', 32' and 34', arranged in first, second and third positions in first and second mirror image halves 40 and 40', respectively, spaced apart along sheet length SL as shown in FIG. 2. In effect, the perforation zones 30, 32, and 34 are arranged in respective first, second and third portions of the strip in a first row in the first half 40, and the perforation zones 30', 32' and 34' are arranged in respective first, second and third portions of the strip in a second row in the second half 40'. A plurality of elongated perforations 28 (shown in FIG. 6) are formed in each of the generally rectangular perforation zones 30, 32, 34, 30', 32' and 34'. Thus, each line in the parallel interior groups of lines in FIG. 2 represents a row of end-to-end perforations such as those illustrated in an enlarged fashion in FIG. 6.

The first perforation zones 30, 30' are each formed with a first plurality of elongated perforations 28 extending in parallel with one another in a first direction 50 parallel to the longitudinal axis of the sheet 11 and nominally designated as 0°. The second perforation zones 32 and 32' are each formed with a second plurality of elongated perforations 28 extending in second and third directions 52 and 54, respectively, at +45°, and −45°, respectively, to the longitudinal axis (the 0° direction 50). The third perforation zones 34 and 34' are formed with a third plurality of elongated perforations 28 extending at 90° to one another in the directions 54 and 52 respectively. In this manner, the perforations 28 in the adjacent perforation zones 32, 32' and 34, 34' are at an angle of 90° to one another and equalize bias forces that arise from the perforation directions 52 and 54 that would tend to cause the sheet 11 to twist when rolled up in the collapsed roll state or as the prosthesis expands to the expanded roll state. Other angles besides 90° may also be used, as long as the longitudinal axes of the elongated perforations are generally symmetric (opposing) across the longitudinal axis to cancel roll bias.

In the illustrated embodiment, each of the three rectangular perforation zones 30, 32, 34 and 30', 32' 34' of the first and second halves 40, 40' are of equal size. The widths of each perforation zones are somewhat smaller than one half the sheet width SW allowing for border and center bands of sheet material. The lengths of each perforation zone along the sheet length SL are substantially the same and are chosen in this case to substantially correspond to the chosen or target circumference of the resulting tubular body in the expanded roll state having substantially three overlapping layers.

The perforation zones 30, 32, 34 and 30', 32' 34' of the first and second halves 40, 40' are formed inside an edge border band 44 extending all the way around the edge of sheet 11 having a width of about 1.2 or 1.3 mm. Similarly, the adjacent perforation zones in each half 40 and 40' are separated from one another by side border bands 45 having a width of about 1.2 mm–1.3 mm. A center border line area 46 of about the same width extends lengthwise down the center of sheet 11 and divides the sheet 11 into the longitudinally extending first and second halves 40 and 40'.

In this manner, the border bands between the perforation zones are preferably minimized, and the first and second pairs of first, second and third zones occupy substantially the entire sheet 11. However, the border bands do prevent the elongated perforations of each zone from encroaching one another or reaching the edges of the sheet 11 to preserve sheet 11 integrity.

Figure 6:
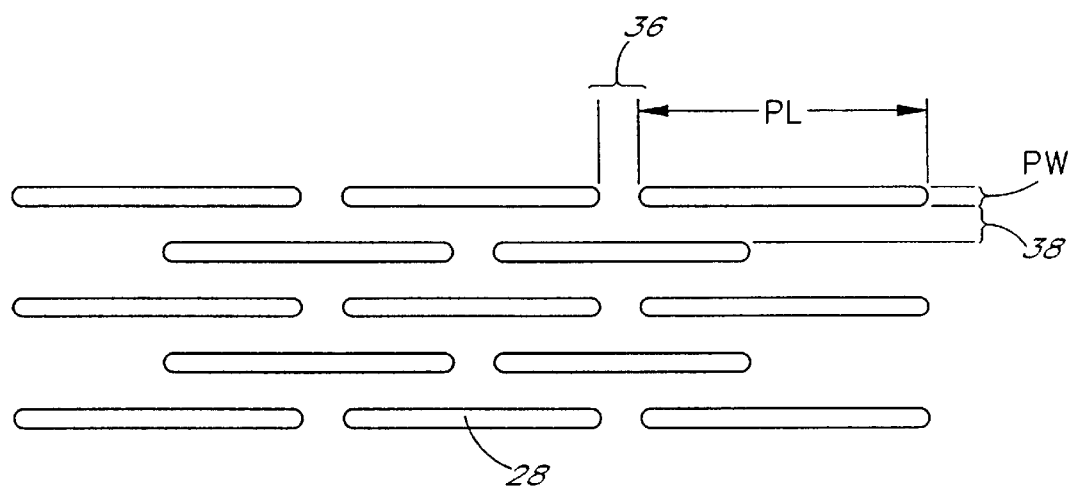
FIG. 6 is an enlargement of a portion of the sheet of FIG. 2, illustrating slot dimensions in accordance with one embodiment of the invention.

Turning to FIG. 6, one perforation pattern of a segment of the plurality of elongated perforations 28 of each zone is shown in enlarged detail. Each elongate perforation 28 is preferably about 1–3 mm in perforation length PL and between 0.10 mm and 0.50 mm in perforation width PW. The end to end and side to side separations 36 and 38 between adjacent perforations 28 is preferably about 0.2–0.5 mm in both cases. The perforations 28 are in parallel with directions 50, 52 and 54 in each of the perforation zones depicted in FIG. 2.

Figure 4:
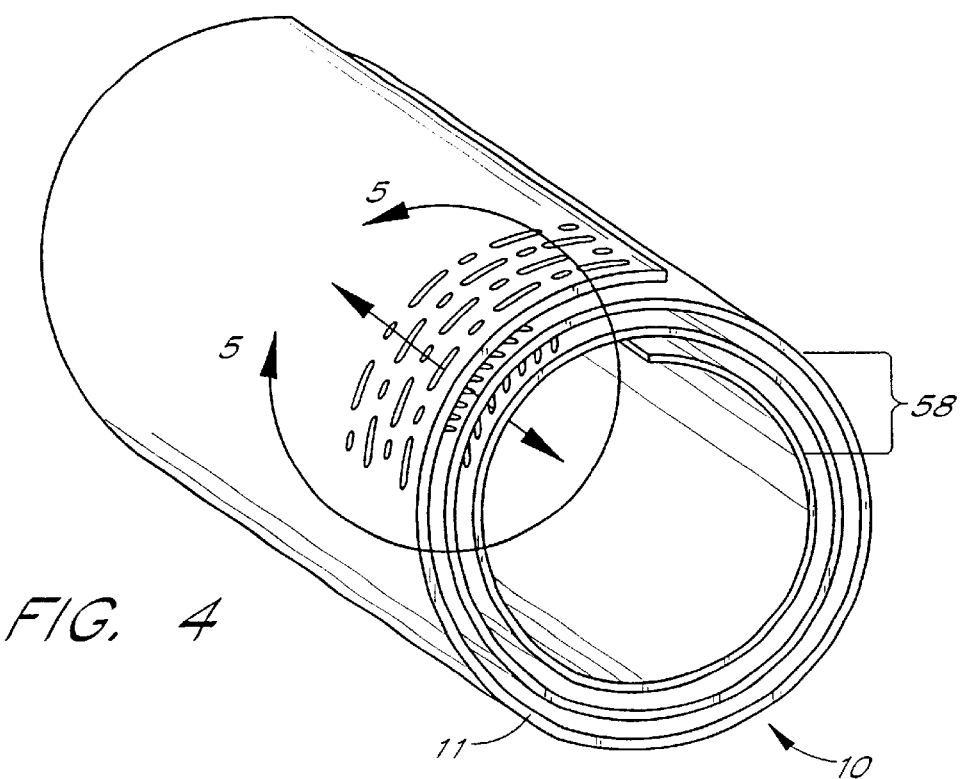
FIG. 4 is an enlarged perspective view of the sheet of FIG. 2 rolled up in a tubular body to form overlapping layers having overlapping zones of perforations.
Figure 5:
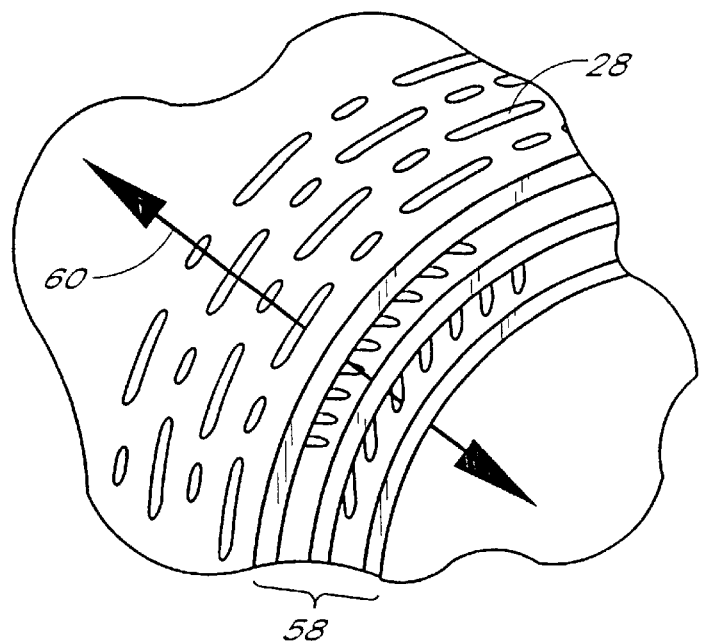
FIG. 5 is a fragmentary enlarged perspective view of a side wall section of three layers of the sheet of FIG. 2 rolled up to overlie one another and depicting alignment of the perforations in the first, second and third perforation zones to provide spaced apart, continuous openings through the side wall.

Turning to FIGS. 4 and 5, the stent 10 of the illustrated embodiment is depicted in one of the possible expanded roll state wherein the sheet 11 is rolled up in the sheet length direction SL in three overlapping rolled up sheet layers which together form the side wall 58 of tubular body 13. Consequently, the perforation zones 30, 32, and 34 in the first half 40 and 30', 32', 34' in the second half 40' overlap one another around most if not all of the perimeter of side wall 58. A portion of the perforations 28 in the overlapping zones 30', 32' and 34' are also depicted in FIGS. 4 and 5 to illustrate the formation and maintenance of openings, e.g., as opening 60, extending through the side wall 58. The alignment of the perforations 28 in each overlapping zone 30', 32', 34' and 30, 32, 34 provides a multiplicity of such spaced apart openings extending completely through the side wall. Given the dimensions and spacing of the perforations 28 stated above, each opening 60 is no greater in size than the perforation width PW. The spacings in the sheet length SL and sheet width SW directions between openings 60 is dependent on the number of layers formed when the sheet 11 is unrolled into the expanded roll state to fit into the vessel lumens.

The spaced apart openings 60 are formed due to the complementary interaction of the first direction 50 with the second and third directions 52 and 54 of the elongated perforations 28 in each overlapping zone. As is evident from FIGS. 4 and 5, the alignment of the zones in the sheet length direction SL and the sheet width direction SW is not critical to the formation of the openings 60. A lateral shift or twist in the rolled up tubular body 13 is tolerable as it still allows the openings 60 to form due to the interaction of the perforations 28 extending at the +45° and −45° directions 52 and 54 in the inner layers with the 0° direction 50 in the outermost layer. The likelihood of twisting is lessened by orienting the perforations 28 in each zone in the mirror image manner depicted in FIG. 2 but may occur to a slight extent.

Although FIGS. 4 and 5 show the tubular body 13 formed of three overlapping layers, it will be understood that the tubular body diameter may be increased or decreased, thereby decreasing or increasing, respectively, the number of overlapping layers, to accommodate a larger or smaller vessel lumen diameter. When the diameter is increased and the tubular body 13 is formed with two overlapping layers (at least in part), the openings 60 may need to be spaced closer together and be somewhat smaller than the openings 60 depicted in FIGS. 4 and 5. When the diameter is decreased to a point where more than three overlapping layers are formed at least in part, the openings 60 may also be spaced further apart and be somewhat larger in size.

In this regard, the preferred embodiment of the stent described above and depicted in the drawings is preferably dimensioned to be used in vessels having a diameter in which the tubular body 13 is accommodated having one and one half, one and three quarters, two, three, four or five or more and any fraction therebetween of overlapping layers in its expanded roll state. A selection of stents 10 may be provided with the sheet length SL and the lengths of the perforation zones 30, 32, 34 and 30', 32', 34' tailored to accommodate a particular range of body vessel lumen diameters. A selection of such stents may also be provided having different sheet widths SW to bridge vascular defects of differing lengths in the body vessel. The physician may select the appropriately dimensioned prosthesis 10 for the particular body vessel.

Preferably the second and third directions 52 and 54 are at +45° and −45°, respectively to the 0° direction 50, and therefore extend to 90° to one another. These angles may also be varied as long as the perforations 28 extending at each angle overlie one another when the sheet 11 is rolled into the tubular body 13 and provide a suitable number of aligned openings 60 through the multiple layers of the side wall.

In the illustrated preferred embodiment, the perforation zones are arranged such that in the first half 40, the first, second and third zones 30, 32, 34 are arranged across the center line border band 46 from the second, first and third zones 30', 32', 34' of the second half 40', so that the second and third directions 52, 54 of the second and third zones 32, 32' and 34, 34' are adjacent to one another across the center border band 46 in order to balance twist biases induced in the sheet 11 by the second and third directions 52 and 54 of the elongated perforations 28. The particular order in which these zones appear from the outer-most to the inner-most layers forming the size wall of tubular body 13 may be changed from the order depicted in FIGS. 2–5. In any such configuration, the sheet 11 may be rolled up such that the first perforation zones 30, 30' are in the inner-most layer rather than the outer-most layer as shown.

Moreover, while the preferred number of perforation zones in each half is three to provide a substantially three layer, tubular body in the expanded roll state, only two or more than three such perforation zones may be provided in each half to provide substantially two or more layers in the tubular body. The case of four perforation zones in each half to provide substantially four layers in the tubular side wall in the expanded roll state, an additional pair of side-by-side perforation zones may be provided both having elongated perforations extending at 90° to the length direction 50 of the sheet.

In addition, the above-described preferred embodiment of the stent of the present invention is provided with perforation zones formed in portions of first and second halves of the sheet on either side of the center line area 46 to thereby form parallel rows of perforation zones along the sheet length SL. It is also contemplated that additional rows of parallel perforation zones may be formed across the sheet width SW and extending the sheet length SL. A selection of directions 50, 52, 54 (or other suitable directions) for each perforation zone is to be made to offset the above described curl bias forces induced by the perforation directions so that the tendency of the sheet to twist out of alignment with the sheet length direction or 0° direction 50 when in the expanded roll state is minimized.

Although the sheet is preferably formed of metal foil, the invention may be practiced using sheets formed of biocompatible plastic materials or other suitable sheet materials.

The prostheses of the present invention may be employed as a graft bridging an aneurysm in a blood vessel and may be employed in the system depicted in the above-referenced '906 application. The prostheses of the present invention may be used in any of a variety of alternative applications where radial support is desired or channeling of blood is desired. Repair of a tear in the intimal wall of an artery or a repair of a dissecting aneurysm is contemplated. The present invention may also be utilized as a stent, such as following radial expansion of a stenosis by balloon angioplasty, laser ablation, rotational atherectomy, or other lesion modifying technique.

Although the above described stent 10 is preferably self-expanding, it will be understood that the perforation zones and complementary pattern may also be used in multi-layer sheet stents that are expanded by an expansion mechanism such as a balloon catheter from the collapsed roll state to an expanded roll state in order to provide the openings 60 through the side wall of the tubular body formed on expansion.

The perforation pattern of the present invention allows the resulting openings 60 to be relatively numerous and small enough to avoid significant blood loss therethrough. Although the present invention has been described in terms of certain particular aperture shapes and patterns, any of a wide variety of aperture size, shape and distribution patterns can be utilized for any of the embodiments disclosed herein, and still accomplish the functional advantages of the present invention. In general, the aperture size and pattern should seek to produce a net aperture through the side wall of the prosthesis which is small enough to prevent substantial blood loss therethrough, and large enough to facilitate endothelial cell growth.

By "net aperture" opening, it is meant the effective cross section of the aperture which has a clear or tortuous passageway through each of the two or three or four or five or more adjacent layers of the sheet when rolled up into the expanded, implanted diameter. Thus, for example, referring to FIG. 5, each slot in each of the three adjacent layers may have a width of about 0.2 mm and a length of about 3 mm. Due to the misalignment of the longitudinal axis of the overlaying apertures, the net opening 60 through the side wall 58 will be on the order of about 0.2 mm in diameter.

In general, net aperture openings of less than about 0.5 mm, preferably less than about 0.25 mm and more preferably less than about 0.10 mm are contemplated. Net aperture openings of about 0.05 mm or smaller may be preferred in some applications. The net aperture opening and aperture density preferably produce a blood or blood serum flow rate through the side wall within the range of from about 50 to about 3000 cc/cm$^2$/minute @ 120 mm Hg pressure. More preferably, the leak rate is less than about 200 and preferably no more than about 100 cc/cm$^2$/minute @ 120 mm Hg pressure. Aperture cross sections for round or nearly round apertures in a microporous embodiment are generally less than about 0.05 inches, often less than about 0.01 inches and is low as about 0.001 inches or less depending upon desired stent performance.

Net aperture dimensions much greater than the recited ranges may also work, but may delay the time until the apertures are sealed off by natural mechanisms. This may be undesirable in an application intended for use as a vascular graft, in which excessive blood loss through the wall of the aperture may be undesirable. In addition, the net aperture distribution should be such that will permit a continuous or substantially continuous layer of endothelial cell growth along the wall of the prosthesis. At the present time, it is believed that the endothelial cell growth will travel no more than about 0.125 inches along a continuous metal surface.

As recited supra., the minimum aperture size should be sufficient to permit endothelial cell growth therethrough. This may be accomplished in apertures having a net cross section measured in microns, with exact limits which can be established through routine experimentation by those of skill in the art. Thus, one hole pattern and distribution pattern for a porous sheet could involve the use of a laser perforation or other technique for producing hundreds or thousands or more of apertures per square centimeter. Distribution may be regular or random, as long as there exists a statistical likelihood that a continuous or tortuous aperture 60 will extend through each of the adjacent wall layers in the expanded, implanted diameter, at a distance of no further apart than about 1/8 or 1/10 of an inch as has been discussed.

One advantage of the aperture configuration and patterns illustrated in FIG. 2, and other pattern designs not specifically illustrated but contemplated herein, is that an appropriate net aperture size will be achieved in the rolled implanted expanded prosthesis, throughout any of a variety of implanted diameters. Since the same stent or graft will optimally be useful in any of a range of vessel diameters, the optimal aperture pattern and distribution will permit the stent to expand from the insertion diameter to any of a variety of implanted diameters which will always achieve a net aperture distribution and dimension in accordance with the foregoing. Thus, the prosthesis of the present invention is expandable from an insertion diameter to any of a variety of implanted diameters and still achieve the endothelial cell growth objectives of the present invention.

As will be appreciated by those of skill in the art in view of the disclosure herein, the embodiments which utilize zones of apertures having a primary longitudinal axis may be provided with any of a variety of orientations with respect to each other. One consequence of certain aperture patterns is the introduction of roll bias in the final product. By roll bias, it is meant the tendency of the stent upon unwinding from the insertion diameter to the implanted diameter to unwind in a manner that spirals out in an axial direction, thereby extending the axial length of the stent. In applications where a roll bias is undesirable, perforation patterns, such as left- and right-hand mirror image patterns, have been found to assist in minimizing roll bias.

For example, although the orientation of the longitudinal slots in the multi-zone embodiment of FIG. 2 are 0° from the longitudinal axis, −45° and +45°, all longitudinal slots may alternatively be provided with the same orientation throughout the sheet. Preferably, to minimize roll bias, at least one zone or a group of zones will have an orientation of −θ to create a first roll bias, and an equivalent zone or groups of zones will have an orientation of +θ, with respect to the longitudinal axis of the sheet to create an opposite roll bias. θ may range from about 10° to about 80°, preferably from about 30° to about 60°, and more preferably from about 40° to about 50° with respect to the longitudinal axis of the sheet. Alternatively, one or more groups of apertures may comprise oval or round holes, rectangular openings, or other geometric configurations, provided that the net aperture size and distribution in the wall of the finished stent when in the intended expanded diameter satisfies the functional requirements described above.

The apertures may be provided in any of a variety of manners which will be understood to those of skill in the art. For example, a sheet of material, such as Elgiloy, or any of a variety of stainless steel or other biocompatible materials having a sufficient spring force is provided. The sheet may then be laser etched, photo etched, perforated using electronic discharge technology or other means, depending upon the sheet thickness, physical properties of the alloy or polymer sheet and desired aperture diameters and patterns. In one embodiment of the invention, the apertures are produced using conventional photo etching technology. The etched sheet is then rolled up and restrained within about a 2½ cm restraining tube, and heated to approximately 900° F. for approximately 4 hours, to relieve stress. In general, the larger the diameter of the restraining tube during the heat stress relief step, the greater the spring force in the finished prosthesis. The heat treated prosthesis may then be tightly rolled and installed within a deployment catheter, or packaged for other use at the clinical site. Prior to loading or packaging, coatings may be added to the tubular prosthesis. Anticoagulants, such as heparin, endothelial cell growth initiators, macrophage inflammation inhibitors or any of a variety of other drugs or coatings, may be utilized, as will be apparent to those of skill in the art in view of the disclosure herein.

Another feature of the prevent invention is the provision of an extremely low leading edge profile in the implanted prosthesis. The leading edge profile, or radial thickness of a prosthesis wall, as seen in a direction of blood flow, is believed to cause undesirable turbulence in the bloodstream. One conventional coronary artery stent, for example, has a leading edge profile on the order of 0.0055 inches. The spiral rolled construction of the present invention permits the use of very thin sheet material, which provides a relatively high radial strength for resistance to radial compression, as a function of total wall thickness. This allows blood flow turbulence to be minimized.

For example, in a stent having a sheet thickness of about 0.0015, rolled up to have three overlapping layers and a net wall thickness of about 0.0045 in accordance with the present invention, is expected to have a radial strength in excess of that for conventional nonrolled stents or grafts having a greater wall thickness. In general, radial deformation preferably begins within the range of from about 50 to about 760 mm Hg global radial pressure. Sheet thicknesses as low as 0.001 inches, and preferably as low as 0.0005 or less (to produce a leading edge profile of 0.0015 inches or less in a three layer as implanted prosthesis) are contemplated by the present inventor.

In accordance with an alternate embodiment of the present invention, the leading edge profile can be reduced by staggering the axial ends of the layers of the tubular stent. Thus, when the stent is rolled up into its normal expanded configuration within the vessel, each internal rolled layer is slightly inset from the previous layer thereby creating a stepped path for the blood interface rather than the full frontal face of several layers stacked on top of each other. This can be accomplished several different ways, as will be apparent to those of skill in the art in view of the disclosure herein. For example, tapering the unrolled sheet width such that it does not correspond to a regular rectangle can produce a stair step leading edge when in the rolled configuration. Alternatively, the sheet can be predisposed to roll into a slight telescoping configuration, thereby achieving a stepped leading edge profile.

Thus, for a three layer stent constructed from a sheet having a thickness of 0.001 inches, the leading edge profile can be reduced from 0.003 inches in a nonstepped configuration to three separate 0.001 inch steps. Each step can be axially spaced apart from the other step by any amount determined clinically desirable, such as within the range of from about 0.001 inches to about 0.01 inches or more. The axial run between adjacent steps can be optimized to produce the least turbulent leading edge profile, yet not adversely affect the structural integrity (eg radial strength) of the stent, as can be determined through routine experimentation by one of skill in the art in view of the particular application for the stent.

In addition, the tubular prosthesis of the present invention provides a relatively uniform leading edge. Many alternate stents and grafts have a jagged or angular leading edge, as a consequence of the wire construction or diamond patterns that may be cut into the wall of the prosthesis. The uniform leading edge is also believed to assist in minimizing leading edge turbulence. Blood flow turbulence may also be minimized, and compatibility of the prosthesis is optimized by the microporous apertures of the present invention, particularly when provided in a density and distribution as discussed above. The facilitation of a continuous endothelia cell coat along the interior wall of the stent is believed to make the stent appear to the blood and surrounding tissue more biocompatible than the material of the stent may otherwise appear to be.

Another advantage of the rolled foil design is that it spreads the radial force of the stent evenly over a large percentage of the vessel wall thereby reducing the localized stress on the medial layer and therefore it reduces or eliminates stress induced inflammation. It has been demonstrated in canine models (UCLA canine study #97097), under the direction of the present inventors, that a 16 mm×51 mm rolled foil stent of 0.002 inch thick nitinol, with a slot pattern similar to that described by this application, may be implanted in 6 mm canine femoral arteries for 30 days and cause virtually no inflammation. This is in contrast to balloon expandable stents that may cause severe inflammation of the vessel walls when implanted at high pressure in similar model.

Thus, in accordance with the present invention, the tubular prosthesis has sufficient contact area with the vessel wall to sufficiently distribute radial force from the implanted stent to the vessel wall to minimize the inflammatory response. Generally, the stent contacts in excess of about 50% of the area of the adjacent vessel wall. Preferably, the stent contacts in excess of about 65% or 80% or greater of the adjacent vessel wall. The surface contact area of microporous embodiments can be calculated based upon the aperture sizes disclosed elsewhere herein.

In accordance with another aspect of the present invention, there is provided a method and apparatus for treating a site in a body lumen by deploying a plurality of tubular supports or stents sequentially along the length of a treatment site. Thus, two or more stents can be positioned sequentially one after another directly against the vessel wall, or within a tubular graft as will be discussed in greater detail below.

Multiple sequential stenting in accordance with the present invention can provide a variety of advantages over conventional stenting techniques. For example, although many coronary artery lesions are relatively short (e.g., 1 cm), other vascular treatment sites may be as long as 5 or 10 cm or longer. Conventional balloon expandable stents are normally deployed using a single stent or single articulated stent per balloon catheter. Thus, where multiple stent treatment is desired, a number of separate balloon catheter entries must normally be used. Although longer stents may result in less total number of stents for a given axial treatment length, long stents may be difficult or impossible to navigate through tortuous and/or narrow vasculature. Even with a long stent, the fixed stent length limits clinical judgment. In addition, most or all practical stent designs or articulated stent segments tend to assume a generally linear configuration once deployed and expanded in a vessel. Thus, the expanded stent tends to straighten the vessel which may prevent stenting of lesions located in curved portions of the vessel. In addition, even in a relatively straight vessel, the linear nature of conventional expanded stents produces a risk of injury at the junction between the axial ends of the stent and the vessel wall.

Thus, in accordance with the present invention, a plurality of relatively short tubular stents are deployed one after another along a treatment length of a vessel. The axial length of each stent may be varied depending upon the desired clinical application. For example, in a coronary artery application, multiple stents may each have an axial length of within the range of from about 0.25 cm to about 2 or 3 cm or longer. Although shorter stents may be used in some applications, stents having an aspect ratio of at least about one and often two or more may be desirable. The aspect ratio is the ratio of the length of the stent to the diameter in the expanded configuration, such that a 16 mm axial length stent positioned within an 8 mm diameter vessel exhibits an aspect ratio of two to one. Stents for use in the present aspect of the invention may be but are not necessarily provided with the various aperture patterns disclosed previously herein for, among other purposes, minimizing roll bias. Thus, relatively higher aspect ratios may be desired in tubular stents which have not been patterned to minimize roll bias.

In general, the number of stents delivered in a single procedure at a treatment site will be a function of the length of the treatment site, the length of the individual stents, and the spacing selected by the clinician between adjacent stents. In general, relatively shorter axial length per stent may be desirable if the treatment site is in a relatively curved portion of the vessel, as will be discussed.

Referring to FIG. 7, there is illustrated a schematic cross-sectional view of a multiple stent deployment catheter 120 in accordance with the present aspect of the invention. The deployment catheter 120 comprises a proximal end 122, a distal end 124 and an elongate flexible tubular body 126. In general, a control 128 is provided on the proximal end 122 for manipulating the catheter 120 and controllably deploying one or more tubular stents 130. The stents are illustrated as spaced apart for clarity, but would normally be in axial contact with each other within the delivery catheter.

In general, the elongate flexible tubular body 126 will have an outside diameter within the range of from about 1 mm to about 8 mm and at least one central lumen 132 having an inside diameter within the range from about 0.67 mm to about 7.5 mm. Any of a variety of conventional materials and techniques can be used for producing tubular body 126, as are well known in the catheter construction arts. In general, for coronary artery applications, the tubular body 126 will have an axial length within the range of from about 135 cm to about 175 cm. For peripheral applications, the length of the tubular body will depend upon the distance between the percutaneous or surgical access site and the treatment site. For example, in a femoral-popliteal graft application, the length of tubular body 126 will generally be within the range of from about 50 cm to about 120 cm, and the outside diameter will range from about 1 mm to about 4 mm for a femoral-popliteal application and possibly larger for other applications.

One, and preferably two or more stents 130 are positioned within the distal end of lumen 132. The stents 130 are preferably "self-expanding" such that they are maintained in a relatively small diameter configuration inside of lumen 132 but they expand radially outwardly when released from the catheter. Any of a variety of known self-expanding stents can be used, including spring coil, shape memory metal (e.g., Nitinol) as will be apparent to those of skill in the art. Preferably, however, a rolled flexible sheet type stent will be used.

In one embodiment of the invention, the catheter 120 is preloaded with the desired number of stents 130 either at the point of manufacture, or at the clinical site, prior to positioning within the patient. For example, two, three, four, five, six, seven, eight, nine, or as many as ten or more stents 130 can be positioned within the catheter 120 prior to insertion into the patient.

In one embodiment of the catheter 120, the stents 130 are loaded in a proximal direction into the distal end of the lumen 132. The total number of stents 130 for a given catheter design will depend upon the desired number of stents available for delivery (the clinician may choose not to use all stents loaded within the catheter 120) as well as engineering reasons such as the coefficient of static friction between the stents 130 and the interior wall of lumen 132. In embodiments intended to carry a relatively large number of stents 130, a lubricous coating such as teflon or paralene or others known in the art may desirably be provided on the interior wall of the lumen 132 as well as on the outside surface of each stent 130.

In an alternate embodiment, the lumen 132 has a substantially constant interior diameter throughout the entire axial length of the catheter 120. In this embodiment, the stents 130 can be "breach" loaded into the proximal end of the catheter 120. A pusher may then be utilized to advance the stents either one at a time or as a group distally through the lumen 132 into a deployment zone within the distal end of the catheter 120. For breach loading designs of catheter 120, additional stents 130 may be loaded into the catheter 120 while the catheter remains within the patient. For this purpose, the pusher is proximally withdrawn from the catheter, and additional stents as desired may be loaded into the proximal end of the catheter and advanced distally to the deployment zone. At that point, the catheter is positioned precisely by the clinician and the additional stent or stents may be deployed as desired.

For either the distally loaded stent or particularly the proximal loaded stent embodiments, it may be desirable to seek to minimize friction between the stent and the interior wall of lumen 132. For example, lubricous coatings such as those identified before can be used.

In addition, it may be desirable to rotate the stent within lumen 32, as the stent travels axially through the catheter. From the direction illustrated in FIG. 7a, rotation of the stent 130 is preferably accomplished in a clockwise direction so that the radially outward most edge of the stent 130 trails against the interior wall of the lumen. In this manner, the stent tends to wind more tightly, and friction between the stent and catheter is reduced. Rotation can be accomplished by rotating the core 136, and frictionally engaging the pusher 134 with the stent. Any of a variety of structures for imparting a rotation to the stent 130 can be readily envisioned by one of skill in the art in view of the disclosure herein.

The stents 130 are positioned distally of a deployment surface such as the distal surface of a pusher 134 for advancing the stents 130 distally out of the end of the catheter 120. The pusher 134 is generally connected to or is the distal end of an elongate flexible axial force transmitting structure such as a central core or tubular body 136 which extends proximally throughout the length of the catheter.

Distal advancement of tubular body 136 with respect to the catheter 120 will deploy stents 130 from the distal end of the catheter 120 as will be apparent to those of skill in the art in view of the disclosure herein. In a preferred deployment method, the relative movement between the catheter 120 and core 136 is accomplished by holding the core 136 in an axially fixed position and retracting the catheter proximally until a stent 130 is deployed. Thus, the distal end of the catheter is positioned at the desired location for the distal end of the implanted stent prior to stent deployment.

Alternatively, the tubular body 136 may be replaced by a nontubular push wire, which runs in parallel to the guidewire 138. In an embodiment using a tubular support 136, the guidewire 138 preferably runs axially through a central lumen in tube 136, through pusher 134 and axially through the stents 130.

Preferably, the proximal end of the catheter 122 is provided with a control 128 for controllably deploying the stents 130. Preferably, the control 128 comprises a structure for indexed deployment of the stents 130, such that one stent may be deployed at a time and under the direct control of the clinician. For example, control 128 may comprise a handle 140 and an actuator 142 such as a lever or trigger coupled to a ratchet structure 144. The trigger 142 and ratchet 144 may be calibrated such that a single pull of the trigger 142 deploys a single stent 130. In this manner, the clinician can deploy the stents 130 sequentially while proximally withdrawing the catheter 120 to produce a series of axially adjacent deployed stents.

Alternatively, the tubular body 136 can be provided with a plurality of visual indicia such as index lines, which are visible to the clinician on the proximal end of the catheter 120. The clinician can manually advance the pusher 134 distally with respect to the proximal end 122 of the catheter 120 to deploy stents 130 as desired. Any of a wide variety of alternate deployment control structures can be readily designed, as will be apparent to those of skill in the art in view of the disclosure herein.

Referring to FIG. 8, there is illustrated a plurality of stents 130 deployed serially in a curved portion of an artery 146. The number of stents 130 used to treat a given axial length treatment site is largely within the judgment of the clinician, depending upon lesion morphology and other considerations. For example, a lesion or other treatment site having an axial length of about 12 cm to 14 cm may be treated using five 2 cm stents having a space between stents within the range of from about 0.1 cm to 1 cm. The spacing between adjacent stents can be varied considerably depending upon clinical judgment. In addition, the present invention permits the spacing of adjacent stents in a manner that prevents occlusion of branch arteries such as branch artery 148 illustrated in FIG. 8.

Referring to FIG. 9, there is disclosed one embodiment of a tubular graft and deployment catheter 160 such as might be used for a transluminal grafting procedure. The catheter 160 generally comprises an elongate flexible tubular body 162 having a proximal end 164 and a distal end 166. Proximal end 164 is provided with a manifold 168 containing appropriate connectors as may be desired in view of the functionality of the catheter 160. For example, an access port 169 is preferably axially aligned with the catheter 160 as is known in the art for receiving a guidewire 182. Access port 169 is also provided with a stent deployment actuator 178, which may be manipulated to deploy stent 172 from the distal end 166 of the catheter 160. Deployment actuator 178 may comprise a plate 180 such as a radially outwardly extending annular flange attached to a push wire or tube 181. In one embodiment, the distal surface on plate 180 is spaced proximally of the access port 169 by a sufficient distance that advancing plate 180 distally into contact with port 169 provides sufficient travel to deploy a single stent 172 from the distal end of the catheter. Preferably, actuator 178 is provided with a lumen (not illustrated) to accommodate guidewire 182. Additional access ports such as dye port 171 may also be provided as desired.

In general, the distal end 166 of the catheter 160 is provided with a stent 172 and a flexible tubular graft 176. Preferably, the stent 172 is connected to the graft 176, either at a point beyond the distal end of the tubular body 162 or through one or more side openings on the tubular body 162.

The distal end 166 in the illustrated embodiment is provided with an axially extending slot 170. Slot 170 permits the rolled stent 172 to be positioned within the distal end of the tubular body 162 with a free end 174 of the rolled stent 172 extending through the slot 170. In this manner, the stent 172 can be positioned fully within the catheter 162, and be connected to a graft 176. The graft 176 is connected at its distal end to the free end 174 such as through the use of any of a variety of adhesives, stitching, thermo-bonding, mechanical interfit, or the like. The vascular graft 176 trails proximally along the outside of tubular body 162. Grafts 176 having lengths within the range of from about 2 cm to about 30 cm are contemplated, although other lengths may be desirable depending upon the clinical application. Any of a wide variety of known graft materials, such as dacron or polytetrafluoroethylene, may be utilized, together with any subsequently developed graft materials as will be apparent to those of skill in the art.

Referring to FIG. 11, there is disclosed one embodiment of a distal end for a stent deployment catheter, which can be adapted for use on either the catheter design of FIG. 7 or FIG. 9 above. A generally cylindrical tip 200 is provided with a proximally extending annular flange 202, adapted to fit within the tubular body 162. Proximal flange 202 terminates at its proximal end in a stop surface 204. Stop surface 204 is spaced axially apart from a complimentary stop surface 208 on the axially moveable actuator 206. A guidewire lumen 207 is illustrated extending axially through the actuator 206.

A stent compartment 210 is disposed distally of the actuator 206. As will be apparent to those of skill in the art, the axial length of stent compartment 210 will be a function of the number of stents desirably loaded therein. Similarly, the axial space between stop surface 204 and complimentary stop surface 208 will correspond to the desired axial travel of the actuator 206 to fully deploy the stents contained in stent compartment 210. Any of a wide variety of other specific structures can readily be devised for deploying self-expanding stents from the distal end of catheter 164, 120 as will be apparent to those who have skill in the art in view of the disclosure herein.

In use, a surgical incision or percutaneous puncture is made to provide access to a vessel to be treated. The catheter 162 is thereafter inserted into the vessel and advanced transluminally until the stent 172 is positioned at or beyond the treatment zone from the perspective of the catheter 162. The deployment structure is advanced distally with respect to the catheter 162, so that the stent 172 is deployed from the distal end of the catheter 162. Deployment of the stent 172 from the catheter 162 permits the stent 172 to assume its enlarged radial configuration within the vessel, thereby supporting the tubular graft 176 against the vessel wall. The catheter 162 may thereafter be proximally withdrawn, leaving the graft 176 extending from the stent 172 towards the clinician through the artery or other vessel.

The proximal end of the graft 176 may be secured such as through a surgical attachment procedure as is known in the art. Alternatively, the proximal end 176 may be secured within the vessel through the use of a second expandable stent deployed from the same catheter 162 or a separately introduced catheter. In a preferred embodiment, the catheter 162 contains at least the distal stent 172 and a proximal stent (not illustrated) for supporting the proximal end of the graft 176. Thus, a procedure such as a femoral-popliteal bypass can be accomplished percutaneously in accordance with the present invention without the need for a surgical cutdown and anastomosis.

Figure 12:
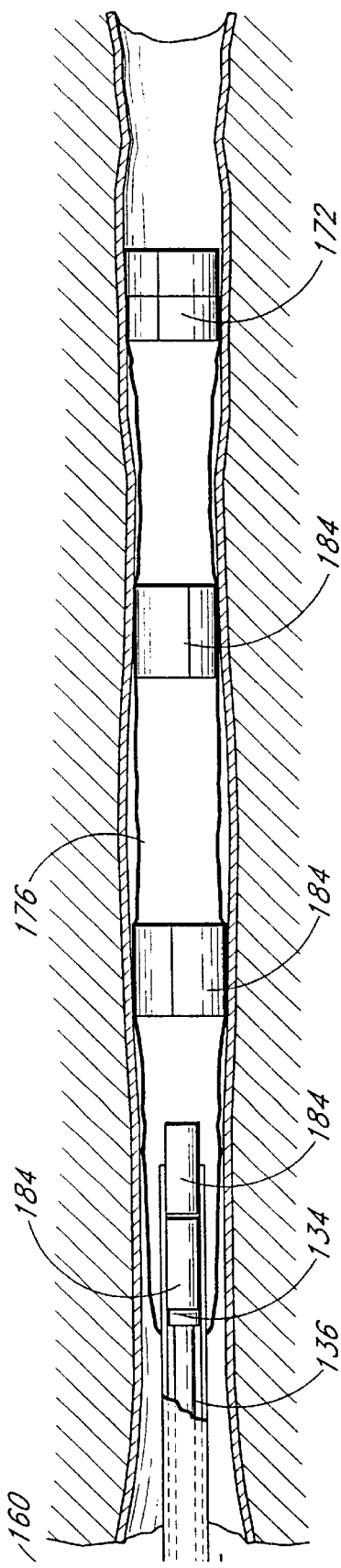
FIG. 12 is a cross-sectional schematic view showing a plurality of tubular supports being positioned within a graft in a body vessel.

In a further embodiment, as illustrated mid-procedure in FIG. 12, the catheter 162 is provided with three or more stents, including the distal stent 172 and two or more additional self-expanding stents. In this manner, the catheter can be withdrawn proximally following placement of the distal stent 172, and one or more stents can be positioned at intermediate locations between the proximal and distal ends of the graft 176. A proximal most stent can be deployed at or about the proximal end of the graft 176. In this manner, a plurality of supports can be positioned within a vascular graft, for providing intermediate support thereby enhancing patency of the graft along its entire length.

The multiple supported graft aspect of the present invention can be accomplished in a variety of ways, depending upon catheter design and clinical preference for a given procedure. For example, the distal stent 172 may be attached to the graft 176 as has been discussed. One or more intermediate supports 184 may also be attached to the graft 176, such as by axially elongating the slot 170 in a proximal direction on catheter 160, as will be apparent in view of the disclosure herein. This design ensures a predetermined spacing between axially adjacent intermediate supports 184 and distal end supports.

Alternatively, the axially spacing between adjacent supports is determined by the clinician during the procedure. In this application, the intermediate supports 184 are positioned within the catheter 160 in a manner described in connection with the catheter of FIG. 7. Thus, axial distal displacement of a stent deployment surface 134 with respect to the catheter 160 controllably deploys the intermediate stents 184.

Depending upon the length of the graft 176 and the spacing between adjacent supports, the clinician may or may not utilize all of the intermediate supports 184 in a given graft implantation. One of the supports 184 will preferably be positioned at or near the proximal end of the graft 176, and will thus become the proximal attachment point of the graft.

In a relatively large vessel procedure, such as a femoral-popliteal bypass, the outside diameter of the catheter 160 is about 2–3 mm and the inside lumenal diameter of an expanded stent 184 will be on the order of about 4–10 mm. Thus, it may be possible for the physician to advance the catheter 160 distally through a previously implanted stent 184 to deploy additional intermediate stents 184 if the physician determines during the procedure that the spacing between adjacent stents 184 was undesirably large. Fluoroscopic or other visualization of the procedure in real time will permit the clinician to deploy a first number of supports 184, evaluate the resulting patency of the lumen, and, if desired, deploy a second support or set of supports 184 as may appear warranted in view of the visualization of the patency of the graft lumen.

Proximal retraction of the catheter 160 following deployment of the distal stent 172 may cause a proximal motion of the graft 176 within the vessel. It may thus be desirable to anchor the distal stent 172 to the vessel wall or otherwise increase the coefficient of static friction between the stent 172 and the vessel wall. Although providing the stent 172 with a relatively larger radially outwardly directed expansion force may accomplish a sufficient anchoring of the stent 172 in the vessel, excess outward force may be medically undesirable.

Figure 13:
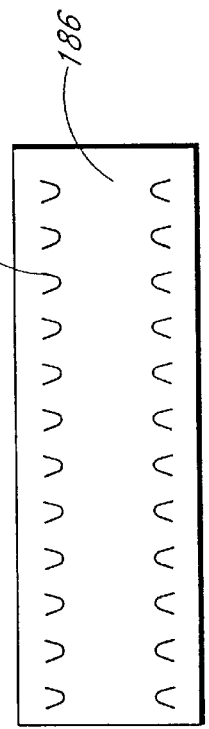
FIG. 13 illustrates an unrolled tubular support of the present invention having a plurality of proximal and distal anchors thereon.

As an alternative anchoring structure, the distal stent 172 and possibly also the intermediate and proximal stents 184 may be provided with a plurality of anchors. Referring to FIG. 13, there is illustrated a flat sheet 186 from which the tubular stents 172 and 184 may be wrapped. The sheet 186 is provided with a plurality of slots or punch-outs 188 throughout at least a portion of the axial length of the sheet 186. Due to the rolled configuration of the sheet (see FIG. 14) in the as-used orientation, in which two or three or more overlapping layers of the sheet 186 will normally be present, anchors 188 need not be provided throughout the axial length of the sheet 186.

Figure 14:
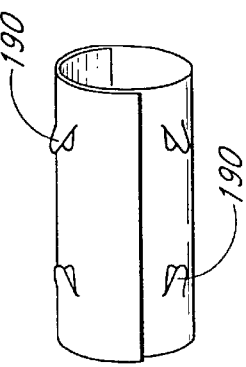
FIG. 14 is a perspective view of the sheet of FIG. 13 rolled into the form of a tubular support.

When the stent is rolled as shown in FIG. 14, the punch-outs 188 will tend to produce a radially outwardly inclined ramp 190 which can be used to anchor the graft 176 against the vessel wall.

A variety of objectives can be accomplished by coating or covering certain surfaces of any of the stents disclosed herein prior to implantation into the vessel. As used herein, the term "coating" is intended to cover generically any form of material which is adhered to or deposited on or adjacent the surface of the stent, such as a jacket or thin film, regardless of the composition, porosity, adhesion characteristics, thickness or biological activity or inactivity of the material.

For example, coatings can be used to affect the physical properties of the stent, such as the spring force or radial strength of the underlying material, or the cross-sectional area of the pores such as in the microporous embodiments disclosed previously. Other coatings can be selected for their biochemical reactivity or stability. For example, coatings which consist of or contain various prostaglandins, cAmp (cyclic AMP), aspirin, coumadin or heparin may be useful to inhibit platelet adhesion or reduce thrombogenicity. Other coatings may be selected to stimulate or inhibit neointimal growth, inhibit restenosis of other etiology, or accomplish other physical or biological activity-based results. Coatings as contemplated herein can be permanent, bioabsorbable, or otherwise transient in the intended use (aqueous/blood) environment.

Figure 15:
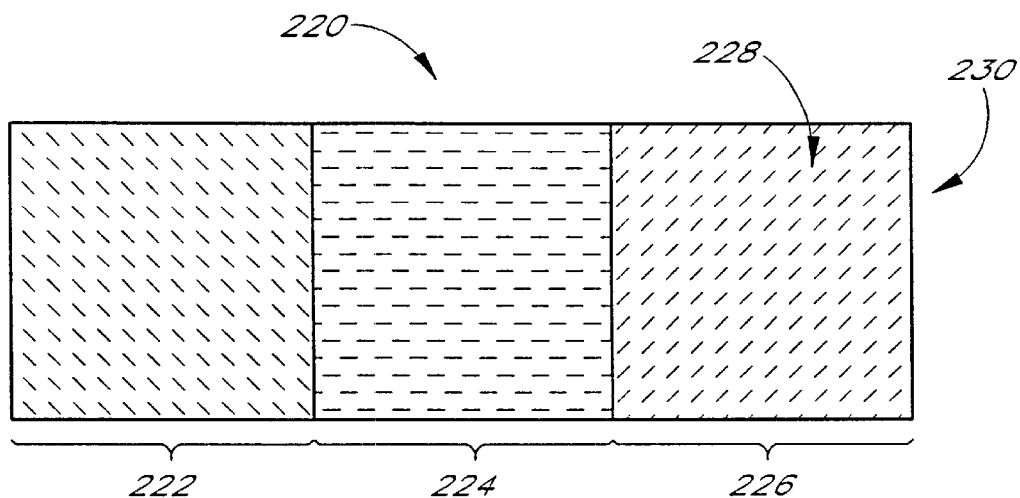
FIG. 15 is a schematic view of an unrolled sheet for construction into a tubular prosthesis.

Referring to FIG. 15, there is disclosed an unrolled sheet 220 of the type which can be rolled into a tubular stent or prosthesis, as has been previously described. The sheet 220 can have a slotted aperture pattern, or randomly or regularly arranged round or irregular apertures as may be desired.

Although the sheet 220 will be described in terms of a stent which has approximately three overlapping layers in its implanted (in vivo) configuration, a three-layer structure is merely one example of the applicability of the present invention and is not intended to limit the scope of the invention to any particular number of overlapping layers. Instead, the description of the three-zoned embodiment of FIG. 15 serves to illustrate the three conceptual zones on a stent of the type disclosed herein, which has at least some overlap in the implanted configuration. The actual stent as expanded in vivo may have anywhere from about 1.2 revolutions or 1.5 revolutions to about 3 or 3.5 revolutions. In general, at least about 1.5 or about 2.0 revolutions (2 layers) will be desirable to produce sufficient radial strength, and in some applications, about 2.5 or 3 revolutions will be useful. The minimum number of in vivo layers desired for a given application may be affected by the lubricity of any coatings on the surface of the sheet 220, as will be discussed.

Referring to FIG. 15, the stent 220 can be conceptually divided into three zones. An inner zone 222 forms the inner wall of the stent when implanted. Thus, the inner facing surface 228 of the inner zone 222 will be in contact with blood or other body fluid in the vessel.

An intermediate zone 224 will exist in any stent having more than 2.0 revolutions in the in vivo configuration. At least a portion of the interior surface 228 and of the exterior surface 230 of an intermediate zone 224 is shielded from direct contact with either blood flowing through the vessel or the vascular wall. Any contact between the intermediate zone 224 and blood or tissue in a full 3.0 revolution implanted stent will typically be limited to whatever biological or chemical contact may be made through the pores or apertures in the adjacent inner zone 222 or outer zone 226.

Another example of a coating would be the use of this stent to deliver radioactive material to the site of a stenotic lesion. The sheet itself may comprise a radioisotope, or the sheet can be coated, clad, or implanted with a radioisotope. There are ample examples in the published literature of the preventative effects of irradiating smooth muscle to prevent the occurrence of restenosis. The problem has been the delivery of the radioactive particles to the site of the potential lesion. Radioactive rays such as gamma rays are so potent that they go through almost anything but thick lead and are therefore difficult to handle and deploy. Beta rays penetrate only very short distances and therefore must be almost in direct contact with the surface to be treated. BES devices that have been used to try to deliver radioactivity have not been successful because the radioactive struts of the BES device are sufficiently far apart from each other that they leave a blank spot in the area between struts. The microporous rolled foil stent on the other hand provides an ideal vehicle for delivering radioactive particles such as alpha or beta rays. For example, a sufficient length of the sheet to equal one circumference in the expanded state (e.g. the outer ⅓ or ½ of the 3 or 2 layer rolled foil stent) could contain the radioactive material. Upon deployment at a lesion the outer layer of the stent would reside against the arterial wall and deliver the radioactivity directly to the area in apposition to the stent. The inner layer or layers of the stent would act as a radiation barrier and protect the blood from unnecessary radiation contamination. The nature and density of the inner layers of the stent material may even reflect a portion of the radiation back to the vessel wall. In either case be it absorption or reflection of the radioactive rays, the protective inner layer of this multi layer stent design will allow higher and more uniform radiation doses to be delivered to the vessel wall than would otherwise be acceptable to an open structure BES type stent or single layer foil stent.

The preferred radioactive coatings are comprised of one or more layers of materials placed upon the stent which serves as the substrate 310, as shown in FIGS. 20A–20D. There may or may not be a clear visual or physical distinction between the various layers in the coating because each layer need not be a discrete structural element of the coating. As the layers including the layer formed by the stent itself bond together to form the coating, they may become blended, alloyed or intermingled to form what looks and acts like a single layer having a somewhat heterogeneous composition. For this reason, the various layers as defined and used herein are intended to denote the functional characteristics of the components or help denote what process steps are used in their formation, whether through the use of discrete structural layers or layers blended with neighboring layers, the selection of which will be apparent to those of skill in the art in view of the particular materials and components used.

The radioactive coatings all comprise an isotope layer 312. The isotope layer 312, comprises metal salt wherein a plurality of the ions in the salt are radioisotopes. The radioisotope can be almost any species available, such as alpha, beta or gamma emitting, as is discussed below. The isotope layer 312 may further comprise one or more metals from which the metal salt of the layer is derived. The isotope layer preferably has a density in the range of $10^{10}$–$10^{25}$ atoms/cm$^2$, more preferably about $10^{13}$–$10^{15}$ atoms/cm$^2$, most preferably about $10^{14}$ atoms/cm$^2$ and is has a thickness of preferably 10014 10,000 Angstroms thick, more preferably about 500–1500 Angstroms thick.

As used herein, the term "metal salt" refers to a compound comprised of at least one anion and at least one cation. The anions and cations of the metal salt may be either simple (monatomic) ions such as $Al^{3+}$, $Cl^-$ and $Ag^{1+}$, or complex (polyatomic) ions such as $PO_4^{3-}$ and $WO_4^{2-}$. At least one of the ions in the metal salt compound should comprise a metal. The term "metal" as used herein means all metals, including, for example, semimetals, alkali metals, and alkaline earth metals. Preferably metals are selected from the transition metals or main group of the Periodic Table of the Elements. The term "metal salt" as used herein in its broadest sense can encompass metal oxides.

Preferably, the isotope in the isotope layer is selected from the group of gamma emitters with energies less than about 300 keV including I-125, Pd-103, As-73, and Gd-153, or the high energy beta group ($E_{max}$>1.5 meV) including P-32, Y-90 and W/Re-188. Other isotopes not currently mentioned, can be utilized by the invention described herein. The selection of these isotopes, however, allows the source to be shielded in a material such as leaded acrylic in commercially available thickness of 15–30 mm, or in a lead tube of approximately 0.3–0.5 mm wall thickness. Some of the other isotopes which may be deemed suitable for use in the present invention or for a particular intended use, include Au-198, Ir-192, Co-60, Co-58, Ru-106, Rh-106, Cu-64, Ga-67, Fe-59, and Sr-90. The selection of an isotope may be influenced by its chemical and radiation properties.

The radioactive coatings of the present invention may further comprise at least one tie layer 311. The tie layer 311 lies between the stent substrate 310 and isotope layer 312 and may act to increase the tenacity of attachment of the isotope layer 312 to the stent substrate 310. The tie layer 311 may comprise adhesives, chemically activated surfaces, a chemical coating layer, an organic or inorganic compound, metal, metal oxide, metal salt, or metal alloy. Preferably the tie layer 311 is 100 to 10,000 Angstroms thick, more preferably 200 to 500 Angstroms.

The radioactive coatings of the present invention may further comprise one or more coating layers 314. The coating layer 314, may act as a sealing means to protect the isotope layer from mechanical abrasion or other injury which may strip the isotope layer of radioisotopes and thus reduce its activity. Furthermore, the coating layer may inhibit migration or other leaking of isotope in an aqueous (blood) environment. Addition of a coating layer may provide sufficient protection for the device to be classified as a sealed radiation source, i.e. one that has less than 5 nCi of removable activity. Each coating layer is preferably 1–30 μm thick, more preferably 10–20 μm thick.

The coating may be a metal or plastic. Plastic coating materials are preferably biocompatible, but not excessively biodegradable. Preferred materials include cyanoacrylates, acrylics, ethylene methyl acrylate, ethylene methyl acrylate/acrylic acid (EMA/AA), urethanes, thermal plastic urethane (TPU), PBVC, PVDC, and the like. Metal coatings can be used as well, with metals used preferably being bio-stable, such as titanium. For example, platinum, gold, or titanium may be vapor deposited on a surface to encapsulate the isotope layer.

Figure 20A:
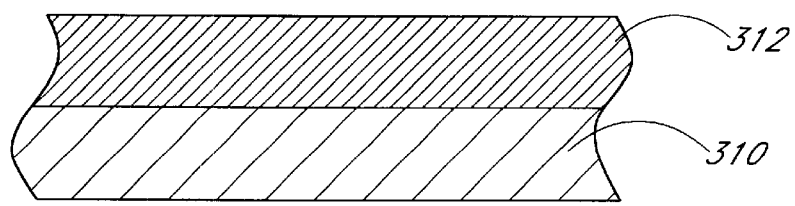
FIG. 20A is a schematic of a cross-section of one embodiment of the vascular liner of the present invention having a radioactive coating thereon comprising a substrate layer, formed by the vascular liner and an isotope layer.

Referring to FIG. 20A, a schematic of a cross-section of one embodiment of radioactive-coated stent is shown. An isotope layer 312 is disposed on the stent substrate 310.

Figure 20B:
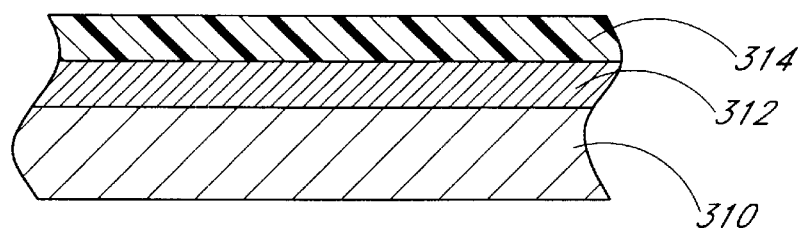
FIG. 20B is a schematic of a cross-section of another embodiment of a radioactive-coated vascular liner of the present invention, wherein the coating has a substrate layer formed by the vascular liner, an isotope layer and a coating layer.

Referring to FIG. 20B schematic of a cross-section of a second embodiment of radioactive-coated stent is shown. The bottom layer is the stent substrate 310, the second or middle layer is the isotope layer 312, and the outer layer is the coating layer 314.

Figure 20C:
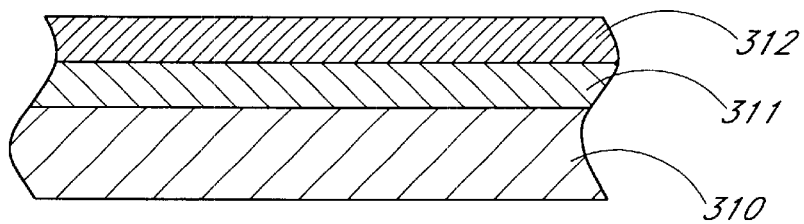
FIG. 20C is a schematic of a cross-section of another embodiment of a radioactive-coated vascular liner of the present invention, wherein the coating has a tie layer formed by the vascular liner disposed between the substrate layer and the isotope layer.

Referring to FIG. 20C schematic of cross-section of a third embodiment of the radioactive-coated stent is shown. The bottom layer is the stent 310, the second or middle layer is the tie layer 311, and the outer layer is the isotope layer 312.

Figure 20D:
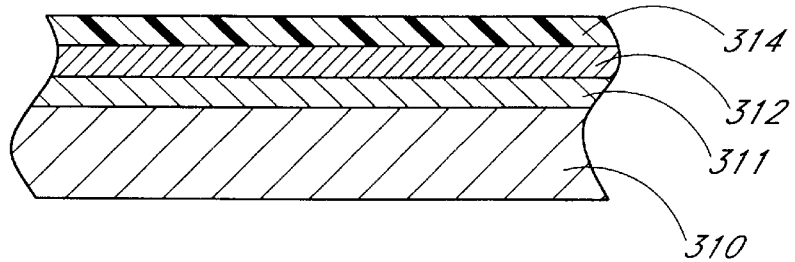
FIG. 20D is a schematic of a cross-section of another embodiment of a radioactive-coated vascular liner of the present invention, wherein the coating has a substrate layer formed by the vascular liner, a tie layer, an isotope layer and a coating layer.

Referring to FIG. 20D, a schematic of a cross-sections of a fourth embodiment of the radioactive-coated stent of the present invention is shown. This embodiment comprises the stent substrate layer 310, tie layer 311, isotope layer 312, and coating layer 314.

Some of the difficulties associated with a lack of consistent dosing which is found with radiation delivery stents of the prior art, as discussed above, could be overcome through the use of longer half-life isotopes. Compared to the example above wherein three stents were implanted with P-32 to a level of 10 μCi using the Hehrlein method resulting in a dose variation of 29% at 7 days and 50% at 14 days, for stents implanted with an isotope with a 60-day half-life, the dose variation between maximum and minimum over the fourteen-day time frame would be reduced to 15%, and over a 7-day period to just 8%. The total dose for the longer half-life isotope will be greater, however the effective dose and dose rate remains to be determined. It is generally known that radiation dose can be increased if it is fractionated, or given over extended periods. Only experimentation can answer this question. However, if a long half-life isotope eventually proves effective, the lowest amount of radiation required to perform treatment is always preferable to any higher amount for safety reasons.

In general, the desired dose appears to be at least about 40 Gray within the first five half-lives of implantation, delivered to a depth of about 1 mm into the vessel wall, or about 20 Gray delivered to a depth of about 0.5 mm into the vessel wall, along the entire length of the source. That implies an activity of about 1 microCurie per centimeter length of stent. The dose may range as high as about 500 Gray at a depth of about 0.5 mm in five half-lives of implantation, along the length of the stent, or an activity of about 25 microCuries per centimeter of stent length. Ideal dosing for a particular clinical environment can be determined through routine experimentation by those of skill in the art, and may in certain applications fall outside of the foregoing ranges. Advantageously, the isotope attachment of the present invention permits the present invention to accommodate any of a wide range of desired dosing capabilities as will be appreciated by those of skill in the art in view of the disclosure herein.

Activity and lifetime of sources can be manipulated by the choice of isotope. The relatively rapid time of decay and concomitant loss of "strength" of short half-life isotopes may present product problems in addition to manufacturing problems. Because the isotope is contained on an implanted substrate and has a short half-life, a lack of consistent dosing may result. Take for example, P-32 implanted on three stents at the same time to a level of 10 μCi using the method described in the above-cited paper by Hehrlein (*Circulation*, 1996). Assume all stents are prepared and available for implantation on day 0. If the first stent is implanted immediately, the second after 7.1 days (one half of a half-life), and the third after 14.3 days (one half-life), then the total dose delivered by the second and third stents, as compared to the first stent, is 29% less for the second stent and 50% less for the third stent. It should be pointed out that the standard of practice for allowable variation in administered dose is 10%.

The radioisotopes used in the radiation delivery sources of the present invention may be beta or gamma emitters, or both, and may have any of a wide range of half-lives, both long and short. The particular isotope, as well as the concentration of the isotope in the source which determines the dose, can be chosen by one skilled in the art to serve the needs of a particular application. In a recent paper presented by Howard Amols at the January 1998 Scripps Clinic Conference on Intravascular Radiation Therapy entitled "Choosing the Right Isotope: What's New? Insights into Isotopes or Why Is it so Hard to Find the Ideal Isotope?," the author states that the best isotope choice from the perspective of both physics and dosimetry would be a photon source with an energy greater than 3 MeV and a half-life greater than 7 days. Shirish K. Jani, in a lecture entitled "Does the Perfect Isotope Exist?" at the same conference states that the perfect isotope for vascular brachytherapy would exhibit a low dose gradient, low dose levels to surrounding body tissues, manageable radiation exposure levels around the patient and a long half-life. Iodine-125 (I-125, half-life 60 days) and tungsten-188/rhenium-188 (W/Re-188, half-life 70 days) are candidates to meet these criteria, and also have long half-lives, and thus are two especially preferred radioisotopes for use in the present invention. Preferred radioisotopes used in the radiation delivery sources of the present invention may be purchased from Oak Ridge National Laboratory (Oak Ridge, Tenn.), New England Nuclear (NEN) or any other commercial suppliers of radioisotopes.

Preferred methods of making the isotope layer of the coating of the present invention may begin with either a stent substrate to be coated directly or a tie layer to which the isotope layer is to be bound. Preferred methods comprise exposing surfaces to fluids comprising reactants or isotopes. Such fluids may be gaseous (including plasma or vapor) or liquid (such as solutions), with liquid solutions being preferred. As such, the methods below are described in terms of liquid solutions.

Preferred methods of making the isotope layer of the radioactive coating of the present invention comprise, in part, either one or both of the following solution processes: (1) oxidation in an acidic solution to form a metal salt from a metal; and (2) ion exchange wherein ions at or near the surface of the metal salt are exchanged with those present in a solution. The first process is based on differences in oxidation-reduction potentials, and the second process is based on differences in solubility. These processes will be taken in turn.

In the first process, the equilibrium is driven by principles of oxidation-reduction (redox). A metal, in the form of a pure metal or part of an alloy, may be converted to a metal salt when it is placed in solution comprising an oxidizing agent. Many metals, including those in preferred embodiments discussed below, can be readily oxidized in solution to form metal cations, which may then form salts with anions in solution.

Whether or not a particular reaction of an oxidizing agent and a metal will occur spontaneously can be predicted by reference to a standard table of half-cell potentials such as that in CRC Handbook of Chemistry and Physics, (CRC Press). If the sum of the potentials of the oxidation half-reaction and the reduction half-reaction is positive, then the reaction will occur spontaneously.

For example, it can be predicted that when silver is added to an acid solution of sodium chlorite, the silver will be oxidized. When added to the solution, sodium chlorite ($NaClO_2$) disproportionates to form hypochlorous acid and chlorine dioxide, which is capable of oxidizing silver as shown below:

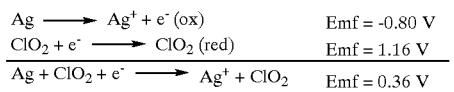

| | |
|---|---|
| Ag $\longrightarrow$ Ag$^+$ + e$^-$ (ox) | Emf = −0.80 V |
| ClO$_2$ + e$^-$ $\longrightarrow$ ClO$_2$ (red) | Emf = 1.16 V |
| Ag + ClO$_2$ + e$^-$ $\longrightarrow$ Ag$^+$ + ClO$_2$ | Emf = 0.36 V |

In addition to the reaction shown above, the hypochlorous acid undergoes a redox reaction whereby chloride ions are produced which then couple with the silver cations to form silver chloride.

The second process is a solubility-driven ion exchange. When, for example, two anions are placed in solution with a given cation, there is a driving force which results in the formation of the metal salt which is less soluble/more insoluble. Because it is difficult to compare solubilities and thus predict behavior when the relative terms "soluble" and "insoluble" are used, solubility is related to a type of equilibrium constant, the solubility product or $K_{sp}$ in order to quantify the degree of solubility for a given compound. The solubility product is equal to the concentrations of the dissociated ions of the salt at equilibrium, that is for salt AB, $K_{sp}=[A^+][B^-]$ wherein $[A^+]$ and $[B^-]$ are the concentrations of the A cation and the B anion, respectively. If a salt is fairly soluble, the concentrations of its component ions in solution will be relatively high, leading to a relatively large $K_{sp}$. On the other hand, if a salt is fairly insoluble, most of it will be in solid form, leading to low concentrations of the ions and a relatively small $K_{sp}$. Thus, when comparing two salts of the same metal, the salt with the lower $K_{sp}$ is the more insoluble of the two. Solubility products for most common compounds can be found in reference texts such as the CRC Handbook of Chemistry and Physics (CRC Press).

The salts silver chloride (AgCl, $K_{sp}=1.77\times10^{-10}$) and silver iodide (AgI, $K_{sp}=8.51\times10^{-17}$) can be used to illustrate the principle of solubility driven ion exchange. The solubility products for these compounds are both fairly low, but $K_{sp}$ for silver iodide is lower by nearly 7 powers of ten, indicating that it is more insoluble than silver chloride. Thus, if solid silver chloride is placed in a solution containing iodide ions, the equilibrium lies on the side of the silver iodide, and the chloride ions will exchange with the iodide ions so that the more insoluble silver iodide is formed. On the other hand, if silver iodide is placed into a solution containing chloride ions, the ion exchange will not take place. In this manner, chloride ions in silver chloride coated on the surface of a substrate can be replaced by $^{125}$I anions to form a radiation source of the present invention.

The metal salt layer which is the starting point for the above solution ion exchange process may be formed by a redox process such as that described above, or it may be applied directly by means of sputtering, vapor deposition, or other techniques known in the art.

Alternatively, if a redox process described above is performed using an oxidizing solution containing a radioisotope, for example $H_3{}^{32}PO_4$, the radioisotope-containing metal salt layer may be obtained directly, eliminating the need for the ion exchange.

Another preferred method for making radioactive-coated stents of the present invention comprises oxidizing a metal, such as those bound to or incorporated in the stent substrate, and then binding an isotope to the metal oxide. The step in which the metal is oxidized preferably occurs spontaneously in air. Thus, metals such as aluminum and copper, which readily and spontaneously undergo oxidation to form their respective oxides, are preferred. Oxide formation occurs when the metal is exposed to air, but may be enhanced or increased by exposure to oxygen-enriched atmospheres or increased temperature. The binding of the isotope is preferably performed by immersing the metal oxide in a solution containing isotope ions, either simple or complex. The attraction between the metal oxide and the isotope ions is such that the isotope ions will bind to the metal oxide rather than existing free in solution. This binding or "plating" process may occur either with or without displacement of ions from the metal oxide.

There are several advantages to using the processes above to place active isotopes on a stent as opposed to the conventional techniques of ion implantation of radioisotopes and nuclear bombardment. One advantage is that unwanted isotopes are not formed. As discussed above with reference to Hehrlein '177, neutron activation of a stent produces numerous isotopes which makes it very difficult to control the dose provided by the stent.

An advantage of the present method is that it does not create large quantities of radioactive waste. By using the correct quantity of radioisotope solution, very little waste is produced. Isotopes which are not incorporated into a given source remain in solution and may be used on another source. Unlike radioactive ion implantation, there is no machine chamber filled with stray isotopes which must be cleaned and safely discarded.

Another advantage of the present invention is that the production process lends itself to batch processing. The attachment of metal layers, such as those which act as tie layers or to which isotopes are later bound, can be done in very large volumes using common chemical attachment techniques found in the semiconductor, solar energy, and packaging industries such as vapor deposition, electrodeposition, ion plating, ion implantation and sputtering. The radioisotopes are most commonly provided in solutions, so the isotope ion exchange or plating step is as simple as soaking the metal salt or metal oxide coated substrate in a solution of isotope. This step can be done in either very small or very large batch sizes, allowing the amount of radiation in the process to be limited accordingly.

Yet another advantage of the present method is that it allows use of isotopes which cannot be readily obtained on a solid source by the other means known in the art. With the proper choice of materials and solutions and the disclosure herein, one skilled in the art would be able to create a reaction scheme to make a salt containing the most of the desirable therapeutic radioisotopes. Furthermore, by using particular long-lived isotopes, a radiation source with a longer half-life can be produced which is capable of delivering a dose with less variation between maximum and minimum. Use of an isotope with a longer half-life may provide for a radiation source which is capable of lowering the amount of radioactivity necessary to perform its function over that which incorporates a short-lived isotope.

Another advantage of the present invention is that the radioisotopes are held by strong atomic-level bonding interactions, and which are highly resistant to leaching or release under physiological conditions. Additionally, the use of ionic bonding is especially useful for radioisotope species such as iodine-125, as the salt form holds the normally volatile iodine atoms in place.

Another benefit to the solution processes described herein is that the density of activity of a given isotope or multiple isotopes may be controlled by simply controlling the time of immersion and/or the density and amount of metal salt or tie layer on the stent.

The basic method, as discussed in part above, comprises providing a stent and forming a coating comprising an insoluble metal salt with at least one radioactive isotope species thereon.

One preferred embodiment of radioactive-coated stent of the present invention is that which has an isotope layer comprising the gamma-emitting isotope $^{125}$I. As mentioned previously, $^{125}$I meets the criteria of an "ideal" isotope as defined by Amols and Jani. One method for making a coated stent having an isotope layer comprising $^{125}$I is that which uses both solution methods discussed above. First, a stent is provided with silver in the metal alloy or elemental silver is attached to the surface of the stent using well-known methods such as ion implantation, vapor deposition, sputtering, electroplating, or rolling. The silver is then converted to silver chloride (AgCl) via an oxidation-reduction solution process such as that described above, which uses an acidic solution of sodium chlorite to reduce the silver and produce silver chloride. Then the silver chloride coated stent is immersed into an ion exchange solution of sodium iodide in the form of Na$^{125}$I, wherein the AgCl is converted to Ag$^{125}$I on the surface of the stent. This manufacturing process may be performed quickly, easily and efficiently. In addition, the 1-125 with a half-life of 60 days would provide an equivalent or lower dose of radiotherapy for a longer period of time.

As an alternative to the above method, silver chloride could be directly deposited to the stent surface by means of vapor deposition or other method known in the art, and then immersed in the ion exchange solution containing Na$^{125}$I.

In an experiment done to demonstrate activity which may be achieved by the methods described herein, silver foil having a surface area of 4 cm$^2$ was immersed in a solution of 6M HCl and 1M NaClO$_2$ in a 10:1 ratio. A portion of the silver was converted to silver chloride. The foil was then immersed in a bath having about 2 ml of solution. The solution in the bath had about 0.07% Na$^{125}$I in NaI, and was prepared by dissolving 0.5 mg NaI in 2 ml water and adding 4.6 mCi $^{125}$I into solution. Following immersion, the resulting activity of the foil was measured at 2 mCi, which, when the amount of carrier (non-radioactive) iodine is factored in, corresponds to about 10$^{18}$ atoms of iodine attached to the sheet. In a carrier free solution, this number of I-125 ions would result in an activity of 3 Ci per 4 cm$^2$ of substrate. This is 30,000 times the required activity for a 10 $\mu$Ci stent.

Another preferred embodiment of radioactive-coated stent of the present invention is that which has an isotope layer comprising $^{32}$P. A coating having an isotope layer comprising $^{32}$P can be made by methods similar to that described above for $^{125}$I using P-32 in the form of orthophosphoric acid (H$_3$$^{32}$PO$_4$) (New England Nuclear). First, a stent is provided. The stent may be manufactured to contain zinc or a zinc alloy, or it may be coated with zinc or a zinc alloy by vapor deposition or other methods known in the art. The zinc may then be converted to a relatively insoluble salt such as zinc fluoride (ZnF$_2$, K$_{sp}$=3.04×10$^{-2}$) via an oxidation-reduction process similar to that discussed above. The stent is then activated by immersing the zinc fluoride coated stent in a solution containing phosphate ion in the form of $^{32}$PO$_4$$^{3-}$ or a soluble phosphate salt, whereby the more soluble fluoride ion is exchanged for phosphate to form zinc phosphate (Zn$_3$(PO$_4$)$_2$, K$_{sp}$=5×10$^{-36}$).

Alternatively, the stent may be directly coated with zinc fluoride or other similarly insoluble salt by vapor deposition or other means known in the art, and then placed in an ion exchange solution. Yet another alternative is to use an oxidizing solution containing H$_3$$^{32}$PO$_4$ so that the zinc is directly converted to zinc phosphate containing the radioisotope, thus eliminating the ion-exchange step.

There is an additional advantage to using Zn$_3$($^{32}$PO$_4$)$_2$ in the isotope layer. Zinc phosphate is a stable molecule and is often used in the automotive industry for paint adhesion to galvanized steel. Zinc phosphate has anticorrosive characteristics of its own, and has been used in the past to increase the corrosion resistance of steel. A zinc phosphate coating on a steel stent may be an advantage to the stent even in the case that it is not coated by a radioactive layer.

Yet another preferred embodiment of radioactive coating of the present invention is that which has an isotope layer comprising tungsten-188 (W-188 or $^{188}$W) Tungsten-188 undergoes beta decay to become rhenium-188 (Re-188 or $^{188}$Re). Rhenium-188 undergoes beta decay as well, but emits a much higher energy particle than in W-188 decay. The W-188 has a much longer half-life than does Re-188, thus the W-188 almost continuously creates more Re-188. This process is known as "generator," and the generator isotopes are referred to together by the shorthand W/Re-188 to indicate the relationship between the species. Generators are attractive for use in radiation delivery devices because they combine the energy levels of a short half-life species with the durability of the long half-life species. It is a general rule that particle energy and half-life are inversely proportional, and that long half-life species are more economical and practical to work with than short half-life species.

W/Re-188 is a beta emitting isotope with an energy about 10% higher than P-32. Where I-125 was discussed as a perfect gamma emitting isotope, W/Re-188 fits the criteria of both Amols and Jani for a perfect beta emitting species for IVRT. The advantage of the W/Re-188 stent would be that the dose would be consistently administered over a long period of time. The half-life of W-188 is 70 days as compared to 14 days for the P-32. This represents a consistent dose rate as Re-188, itself a beta emitting isotope, is being produced by the decay of tungsten for a longer period of time.

Tungsten, in the form of tungstate ion (WO$_4$$^{2-}$) may be readily attached to an oxidized aluminum surface to produce a W/Re-188-containing radiation delivery source of the present invention. An aluminum oxide surface may be attached to the stent by sputtering Al$_2$O$_3$, or Al can be attached by implantation or deposition, followed by an oxidation step. Ambient environment will facilitate the formation of Al$_2$O$_3$ from aluminum which can be accelerated by increasing the temperature and/or using an oxygen-rich atmosphere. The aluminum oxide surface may then be immersed in a tungstate containing solution, such as an acidic solution of sodium tungstate (Na$_2$$^{188}$WO$_4$), in order to attach the W-188 to the alumina surface.

Tungsten may also be applied together with a phosphate in a manner similar to that disclosed by Larsen in U.S. Pat. No. 5,550,006, which is hereby incorporated into the present disclosure by this reference thereto. The method disclosed in Larsen is claimed for use in increasing adhesion of organic resists for printed circuits. The method was used to perform a phosphate conversion coating onto copper. This method may find its application in the radiation delivery device of the present invention in that many polymers and metals other than copper may be coated with this solution. In this method, phosphate may be in the form of $^{32}PO_4^{3-}$, tungstate may be in the form of $^{188}WO_4^{2-}$, or any combination of the isotopes in radioactive or stable form may be used.

Combinations of various isotopes provide another preferred embodiment in that, for example, beta-emitting isotopes may be combined with gamma-emitting isotopes where gamma isotopes can deliver dosage to greater depths.

Radioactive coatings comprising other isotopes can be made by procedures similar or analogous to the preferred embodiments disclosed above, using materials appropriate for the chemistry of the isotope to be included.

In some embodiments of the radiation delivery source of the present invention, it may be desirable to provide a tie layer, onto which the isotope layer can be placed. The tie layer may comprise adhesives, chemically activated surfaces, a chemical coating layer, or an organic or inorganic compound. Preferably the tie layer is a layer of metal, metal oxide, metal salt or alloy. Depositing a metal-type layer may allow an alloying process to take place, which will enhance the tenacity of attachment of the metal salt, and hence the isotope species. This is common in the semiconductor industry, wherein a chromium layer is used as an initial layer in the deposition of gold. The chromium is alloyed with the gold in order to increase the strength at which the gold is bound to the substrate. If, for example, the isotope layer comprises a zinc salt, a metal such as copper or aluminum may be used as the tie layer. The tie layer may also be in the form of an oxide that provides oxygen to chemically bind the atoms of the metal salt layer thereby increasing the tenacity of attachment.

The first metal layer to which the isotope layer is attached may comprise any suitable metal or metal oxide. The layer may be deposited by vapor deposition, sputtering, ion plating, ion implantation, electrodeposition, or other method. When the tie layer is present, there may or may not be a clear distinction between the tie layer and the isotope layer. In performing its function, and depending on the chemistry of the materials involved, the tie layer may become blended, alloyed or intermingled with the isotope layer, thus blurring the lines between the layers. For many of the same reasons, the distinction between the tie layer and a metal-containing substrate layer may also be blurred. In these cases, the term tie layer is meant to be a functional or process-defining definition, rather than a reference to a physically distinct layer of the radiation delivery source.

Although the stents of the present invention may have isotopes which are sufficiently adherent without further treatment, in some embodiments of the present invention, it may be desirable to place an outer coating layer on the stent. An outer coating can provide further advantages for the radioactive-coated stent of the present invention in that the coating can help provide additional means to bind the layers of the source together. Perhaps more importantly, an outer coating can increase the abrasion resistance of the radioactive-coated stent.

Sealed radioactive sources are those which have less than 5 nCi of removable activity. By providing a coating on the stent which covers at least the isotope layer, the source can be protected from unwanted loss of activity due to mechanical abrasion of the surface of the source. This is very important, both for providing safe devices for the patient which leave radioisotopes behind only where they are desired, and for monitoring dosage to ensure that the dose which is to be provided by a stent source will actually reach the treatment site, and not be significantly diminished due to loss of isotope from abrasion which may occur during handling, including implantation. It also helps insure that, once the stent is positioned, the radioisotopes will remain at the placement site and not be washed downstream.

Coating materials are preferably biocompatible, but not excessively biodegradable. Preferred materials include cyanoacrylates (Loctite, Hartford, Conn.), acrylics, ethylene methyl acrylate (Exxon Chemical Co., Houston, Tex.), ethylene methyl acrylate/acrylic acid (EMA/AA) (Exxon Chemical Co., Houston, Tex.), urethanes and thermal plastic urethane (TPU) (BF Goodrich, Richfield, Ohio), PVDC (Saran, Dow Chemical, Midland, Mich.), PBVC, and the like. Other preferred coatings may comprise other biocompatible materials, drugs or similar compounds, such as heparin. Many methods are available to perform the coating process, such as dip or immersion coating, spray coating, spin coating, or gravure. The curing technique may be any of the various techniques available, such as air, heat, or UV. Preferably the thickness of the coating which is formed is 1 $\mu$m to 30 $\mu$m more preferably 10 $\mu$m to 20 $\mu$m.

One preferred embodiment of the present invention has a coating that is formed with cyanoacrylate. Another preferred coating layer is that formed by ethylene methyl acrylate/acrylic acid (EMA/AA). An aqueous dispersion of this coating material, preferably having a viscosity less than 100 centipoise, allows for use of any of the above-mentioned coating methods. UV curable polyurethane acrylate is also useful as a coating layer material. Yet another preferred coating layer is that formed by SARAN. Such a layer may be formed, for example, by immersing the source or a portion thereof into a melt of SARAN or a solution containing SARAN.

The coating layer may also be formed by a spin coating process. Spin coating the thin film source finds advantage in the flexibility to use coating materials having a wide range of viscosities. Low viscosity liquids may be spun on slowly, while a higher viscosity liquid may be spun at a higher velocity to maintain a thin coating. The substrate may be held in place by fixturing or by vacuum during the spin coating process. In an experiment, a dispersion of cyanoacrylate in acetone was dispensed on top of the metal salt surface while the substrate was rotated at 8000 rpm for five minutes. The resulting thickness of the coating was about 6.5 $\mu$m (0.00025 inch). When this specimen, having the spin-coated surface curable coating of cyanoacrylate was extracted in saline for 8 hours at 50° C., the amount of radioactivity extracted was negligible.

An outer zone 226 surrounds the outer surface of the implanted tubular stent, such that an exterior facing surface 230 of the outer zone 226 will be in contact with the vessel wall.

As will be understood by those of skill in the art, in a stent 220 intended for placement in a vessel dimensioned such that the stent will have two complete overlapping layers in the implanted configuration, the central zone 224 will disappear, and the interior facing surface 228 of the inner zone 222 will be in direct contact with the blood, and the exterior facing surface 230 of outer zone 226 will be in contact with the vessel wall.

The unique construction of the rolled multi-layer tubular stent of the present invention permits the inclusion of a coating on the entire sheet 220, or selected portions of the sheet 220, to accomplish any of a variety of objectives. For example, at least the interior facing surface 228 of the inner zone 222, and possibly also the exterior facing surface 230 of inner zone 222, is coated in one embodiment with a biocompatible material to reduce thrombogenicity. Any of a variety of materials, such as Parylene (Specialty Coating Systems, Inc., Indianapolis, Ind., 46241); heparin (such as a photolink heparin coating from BSI Corporation, Eden Prairie, Minn. 55344); PTFE spray, or others as will be understood by those of ordinary skill in the art, can be used. Due to the eventual neointimal growth on the interior surface of the stent, the antithrombogenic coating can be temporary (e.g., roughly on the order of about one to two weeks).

At least the exterior facing surface 230 of the outer zone 226, and possibly also the interior facing surface 228 of outer zone 226, and the entire intermediate zone 224, may be left exposed metal. The contact between the metal exterior surface 230 and the vessel wall may desirably stimulate neointimal growth through the stent.

Thus, the tubular stent formed from sheet 220 can conveniently have a metal outer surface 230 for contacting the vessel wall and stimulating neointimal growth, and a biocompatible coating on the interior facing surface 228 for minimizing the thrombogenicity of the stent.

The rolled configuration of the present invention permits any combination of coated and uncoated surfaces on the finished stent. Thus, the blood contacting surface can be provided with a first coating, and the tissue contacting surface can be provided with a second coating which is different than the first coating. Alternatively, either the blood contacting surface or the tissue contacting surface can be left uncoated while the other surface is provided with a coating. In a stent having an intermediate zone 224, the intermediate zone can be provided on one or both surfaces with a coating, such as to inhibit cellular proliferation, to moderate chemical communication, or other purposes as desired.

The coatings may be applied in accordance with any of a variety of techniques, as will be apparent to those of skill in the art in view of the disclosure herein. For example, the sheet 220 may be dipped into a reservoir of coating or coating precursor material, in an embodiment where at least a portion of both the interior facing surface 228 and exterior facing surface 230 is to be coated. For example, the sheet 220 can be dipped into the coating material to a depth of from about ¼ of the length of the sheet to about ½ the length of the sheet, and preferably in the area of about ⅓ the length of the sheet, such as to coat the inner zone 222 or the outer zone 226. The other end of the sheet can thereafter be dipped into a second coating material, so that the rolled tubular support will have a dissimilar material on the interior surface than the exterior facing surface.

Alternatively, the coating material can be applied such as by spraying the sheet or portions of the sheet, using techniques known in the art. Spraying permits selective coating of one side of the sheet, such as either interior facing surface 228 or exterior facing surface 230 or portions thereof. Through the use of fixturing tools or masking techniques, a portion of one side of the sheet 220 can be coated using spraying techniques. The remainder of the sheet can be left uncoated metal, or can be provided with a dissimilar coating.

In an embodiment where, for example, a bare metal surface desirably is placed in contact with the vessel wall, and a coated surface is desirably placed in contact with the bloodstream, it may be convenient to spray coat the entire interior facing surface 228, even though only a portion, such as inner zone 222, will be in contact with the bloodstream. However, coating on the sheet 220 where it will be eclipsed by an intermediate zone 224, for example, will add unnecessary thickness to the sheet. In general, it is desirable to maintain sheet thickness as low as possible, thereby minimizing the introduction cross-sectional area of the tubular stent. Thus, some estimation of the expanded configuration of the stent (e.g., approximately 0.5 layers overlap, 1 layer overlap, 1.5 layers overlap, 2 layers overlap, 2.5 layers overlap, 3 layers overlap, or other), should be made and taken into account during the coating process so that only a sufficient surface area of the sheet 220 is coated to provide a coating over the relevant surface on the finished stent.

The above-identified coatings may have thicknesses on the order of several molecular layers. In an alternate embodiment, the coating may take the form of a relatively thicker cover such as a film or jacket, such as having a thickness measured in ten thousandths or one thousandths of an inch or greater.

In the thick coating embodiments, the coating can be used to accomplish a variety of physical property objectives, such as controlling the pore size of the microporous apertures through the stent wall. Sheets 220 can be produced using EDM technology having apertures as low as on the order of about 0.001 inches (approximately 25 microns). Smaller apertures can be provided by covering a sheet having relatively large apertures with a coating to produce a reduced aperture size.

Thin films having controlled aperture size for use with this aspect of the present invention have relatively little structural integrity (e.g. PTFE film having a porosity of about 25 to 250 ml of water/Cm2/min @ 120 mm HG pressure, and a thickness on the order of 25 to 50 microns and cannot therefore be conveniently used by themselves in a stent application. However, when applied to the sheet 220 of the present invention the sheet 200 provides sufficient support to produce a functional tubular stent, while the supported film controls the aperture size of the stent. In addition, the film can operate to reduce thrombogenicity or other biological functions. Thin films, such as expanded PTFE film having a thickness lower than about 10 microns and preferably lower than about 5 microns, can be used for this purpose. Generally, aperture sizes in the film are within the range from about 2 to 10 microns.

In accordance with another embodiment of the present invention, the thin film or other coating can be used as an isolation layer to moderate biological communication between the outside and the inside of the tubular prosthesis. For example, a central zone, such as intermediate zone 224 of a microporous sheet 220, may be coated on one or both sides in the flat state with a thin layer (e.g., from about 0.0004 to about 0.006 inches) of PTFE, ePTFE, or other suitable biocompatible isolation material. The covering may be applied in either a complete or partial manner to the inside only, the outside only, or to both sides of the sheet to create the isolation barrier. The isolation barrier separates the flow of blood from the wall of the vessel. In one embodiment, the isolation barrier covering is supplied to the middle 30% to 40% of the length of the sheet 220.

In the deployed in vivo state, the covered stent will isolate the blood flow from the wall of an artery and/or a lesion, aneurysm, perforation, or other defect, with the wall of the artery. In the partially covered isolation layer embodiment, an uncoated microporous foil stent layer is exposed to the arterial wall on the outside of the stent and to the blood flow on the inside of the stent. These uncoated microporous layers allow for neointimal tissue growth and adherence to the microporous surface of the stent, while the isolation barrier reduces or eliminates the stimulation of smooth muscle cell proliferation caused by triggering components within the blood.

Figure 16:
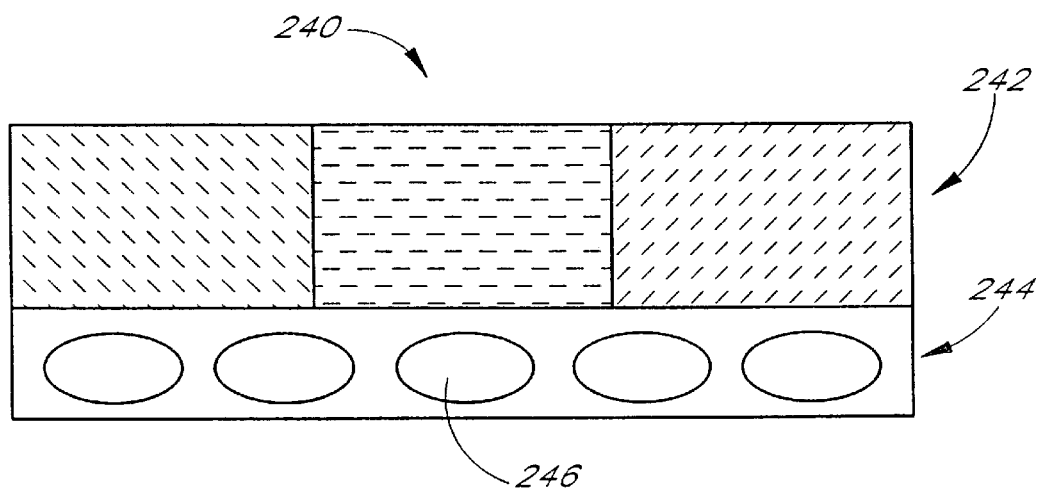
FIG. 16 is a schematic view of an alternate embodiment of an unrolled sheet.

In accordance with another aspect of the present invention, the flexible sheet is configured to permit perfusion through branch vessels, such as the renal vessels in an abdominal aortic aneurysm application. Referring to FIG. 16, there is disclosed a sheet 240 configured to permit branch vessel perfusion. The sheet 240 comprises at least one microporous zone 242 and at least one perfusion zone 244. The microporous zone 242 and perfusion zone 244 are oriented on the sheet 240 such that when the sheet 240 is rolled into a tubular prosthesis, the prosthesis will have a perfusion zone 244 and a microporous zone 242 thereon. In one embodiment, the perfusion zone 244 is disposed adjacent one end of the stent. In another embodiment, the perfusion zone 244 is positioned in between the two axial ends of the stent, and spaced apart from the axial ends of the stent. The precise axial location of the perfusion zone 244 along the length of an implanted stent can be varied, depending upon the intended implanted location of the tubular prosthesis relative to the branch artery.

In general, the microporous zone 242 may have aperture size and/or orientation patterns in accordance with any of the previously disclosed embodiments. The perfusion zone 244 is preferably provided with a plurality of apertures 246 which will generally be significantly larger in diameter than the micropores in microporous zone 242. In this manner, the net aperture size through the side wall of the rolled stent will be sufficient to permit perfusion through the side wall of the stent and down the branch artery. In the illustrated embodiment, the perfusion zone 244 is provided with two or three or more oval apertures having a long axis diameter that is 1.5 to 3 times the diameter of the branching vessel, and a short axis diameter that is 1.25 to 2 times the branching vessel. Alternatively, the apertures 246 can be rectangular, separated by a plurality of transverse struts. Specific aperture cross-sectional areas and patterns can be varied, according to the desired degree of branch artery perfusion, as will be apparent to those of skill in the art in view of the disclosure herein.

In accordance with another aspect of the present invention, there is provided a modification to the rolled sheet to ensure that the ends of the sheet conform to the wall of the cylinder when the stent is implanted in a vessel. See, e.g., FIGS. 17–19. One characteristic of the design of a rolled foil sheet 250, is that the inner and outer terminal ends 252, 254 will separate from the circumference defined by the rest of the rolled sheet unless a modification is made to the spring force (sometimes referred to herein by reference to flexibility) at the terminal ends. The terminal end are defined for this purpose as the area within approximately the last ¼ to ½ inch of either end of the sheet for a foil that is, for example, 0.002 inches in thickness and made from a material such as nitinol or Elgiloy and about 26 to 76 mm long.

Inside the rolled foil, this separation of the terminal end 252 manifests itself as a short segment of stent wall that forms a chord across a section of the circumference of the central lumen of the stent. This chord section may be as much as about ¼ inch in length when the stent is rolled to a diameter of about 8 mm. This chord section creates a small axial channel separate from the central lumen created by placing the stent in a tubular structure such as a blood vessel.

At the outer end 254 of the stent, the terminal end of the foil forms a tangential flap which does not conform to the circumference of the tube when the stent is rolled to a diameter of about 8 mm or less. The flap becomes longer and more acute as the stent is rolled tighter and it becomes shorter and less arcuate as the stent diameter becomes larger. At about 16 mm in diameter the flap almost disappears as the end of the foil conforms to the circumference of the tubular stent. This effect creates a small separation layer when the stent is placed inside a rigid tube or it results in a point of concentrated stress if the stent is placed inside a flexible tubular vessel such as a blood vessel.

The two separation layers described above are a function of the thickness of the sheet material, the modulus of elasticity (Young's modulus) of the material and the radius of the arc around which the foil is to be bent. With two materials of equal modulus of elasticity but different thickness are bent around a similar radius, the thicker material will tend to create a greater diversion from the fixed radius of the tube. If the material thickness is held constant and the modulus of elasticity is varied, the material with the greater modulus of elasticity will form the greater departure from the circumference of the tube and so forth. In this example, the departures from the radius are caused by the action of the spring force within the material used to create the stent. In this example, the material is 0.002 inch thick nitinol. When the stent is rolled up to form a tube, the flat sheet is first flexed into an arc. The lengths of stent on either side of the middle of the arc act as lever arms and the resistance in the middle of the arc acts as a fulcrum. As the arc is progressively formed into a tube the ends will meet. As one end overlaps the other end, a spiral tube is formed. As the diameter of the tube decreases and the ends are continuously wrapped around the tube to create multiple layers, the lever arms are continuously shortened. As long as the lever arms are sufficiently long to overcome the spring force of the material created by the arc, or the arc is sufficiently large that the spring force is negligible, then the material will take the shape of the established arc and a spiral tube will be formed with multiple apposed layers. When the lever arms become too short to overcome the spring force of the material, or the radius becomes sufficiently short that the spring force increases beyond what the lever arms can overcome, then the ends will depart from the radius defined by the tube and create the chord section and flap at the terminal ends as described above.

Figure 17:
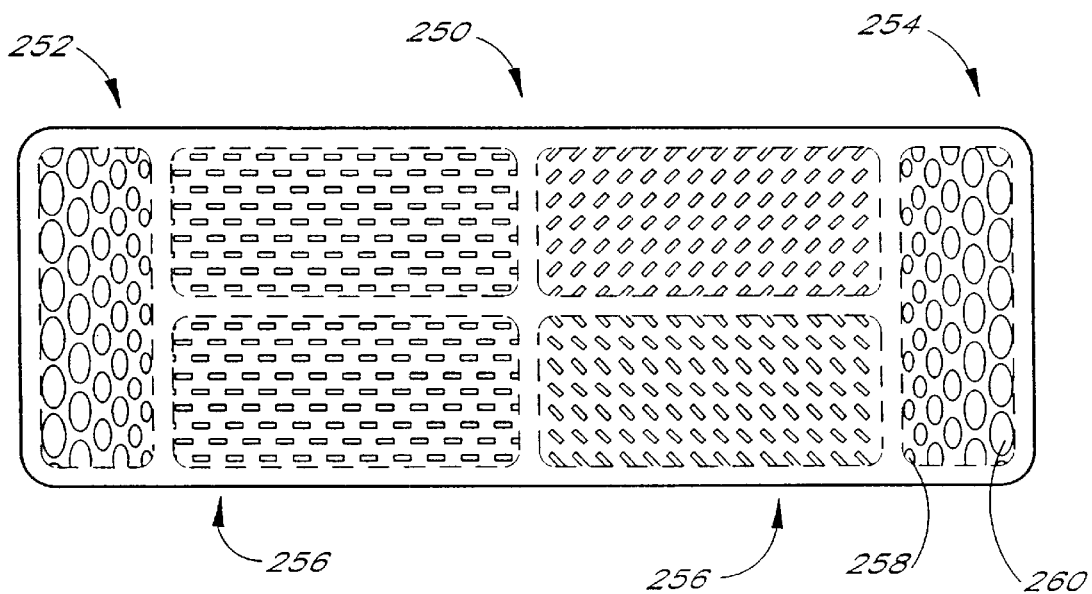
FIG. 17 is a schematic illustration of a sheet in accordance with the present invention having modified terminal ends.
Figure 18:
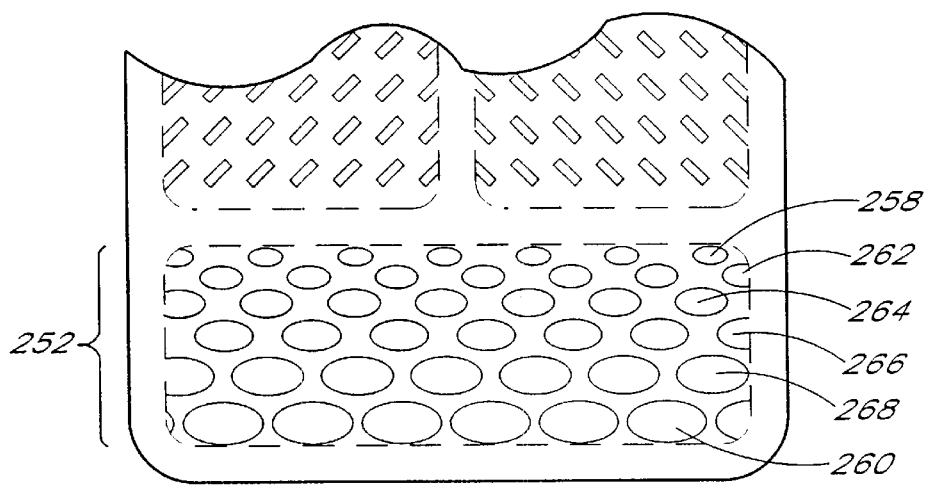
FIG. 18 is an enlargement of one of the terminal ends of the sheet illustrated in FIG. 17.

Any of several structures which proportionately reduce the spring force near the ends 252, 254 of the foil as the lever arms are shortened, will allow the terminal zones or ends to more closely approximate the curvature of the defined tube. In the embodiment of FIGS. 17 and 18, the sheet 250 has a cross-sectional metal content of approximately 67% at a reference point 256 just prior to the defined terminal ends 252, 254. The sheet 250 has terminal ends 252, 254 that contain elliptical holes which become progressively larger as each row of holes approaches the corresponding end of the sheet. The first row 258 of elliptical holes represents about a 65% metal content; the last row 260 of elliptical holes represents about a 38% metal content.

Referring to the embodiment illustrated in FIG. 18, each of the apertures in the terminal zone or end 252 (or 254) is a generally elliptical hole having a length which is about twice the dimension of the width. The aperture centers in each row are spaced approximately 2.00 mm apart along a plane which is transverse to the longitudinal axis of the sheet. The apertures in the least flexible row 258 have a width of about 0.4 mm, and the apertures in the most flexible row 260 have a width of about 0.9 mm. The apertures in row 262 have a width of about 0.5 mm, row 264 have a width of about 0.6 mm, 266 have a width of about 0.7 mm, and 268 have a width of about 0.8 mm. The length of the zone 252 is about 5.3 mm on a sheet 250 having an overall length of about 51 mm, and a width of about 6.0 mm. That particular embodiment comprises a nitinol sheet having a thickness of about 0.002 inches (0.051 mm).

As more and more metal is removed from the terminal ends, the spring force is diminished proportionately. For this example, the progressive reduction in spring force at the ends allows the stent to form a more perfect cylinder when rolled into a diameter of 6 to 8 mm. These terminal end sections may be longer for thicker metal, higher modulus of elasticity, or for a tighter radius in proportion to the changes is lever arm length. Conversely, more metal may be removed at a higher rate to achieve even more compliance with the desired radius.

Figure 19:
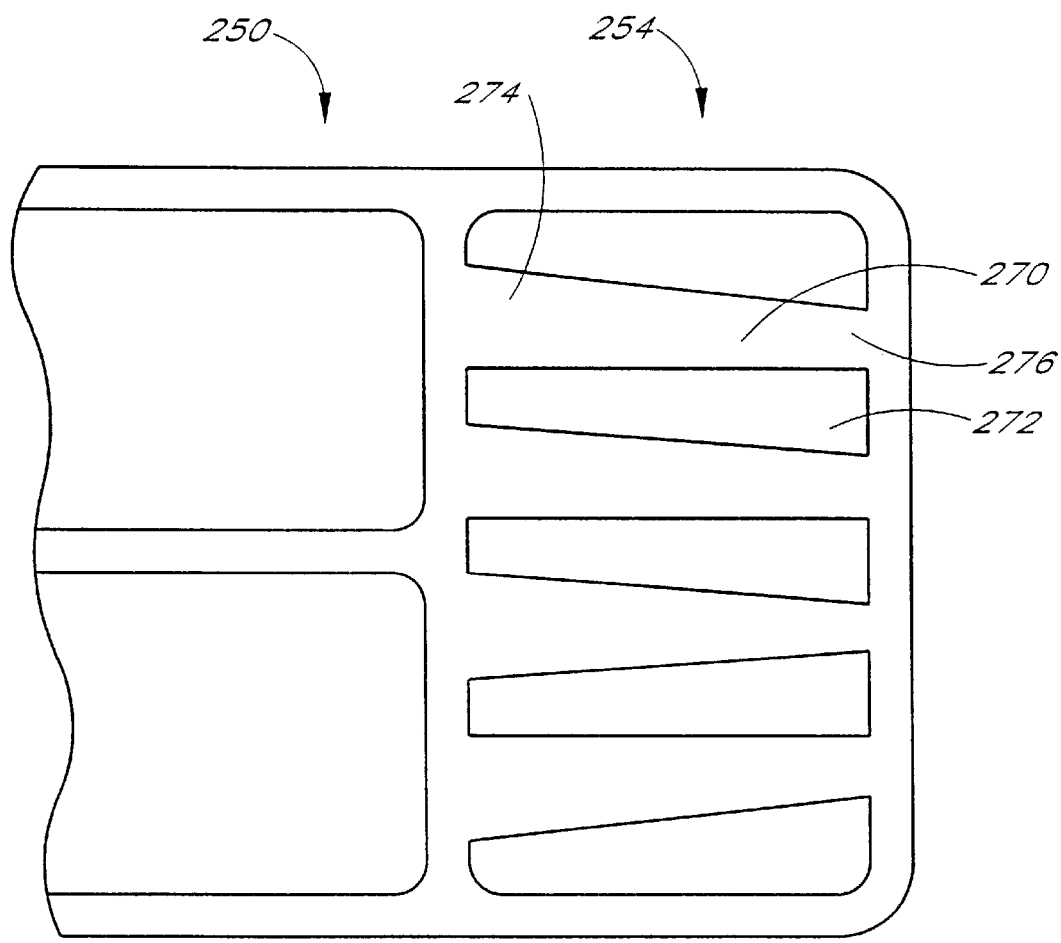
FIG. 19 is an alternate embodiment of a modified sheet end.

FIG. 19 illustrates an alternate embodiment of the design. The terminal end 254 on sheet 250 is provided with a plurality of axially extending supports 270 which are spaced apart to provide a plurality of apertures 272. The support 270 in the illustrated embodiment tapers from a relatively larger width at a first end 274 to a relatively smaller width at a second end 276 proximate the end of the sheet. In this manner, the aperture 272 is provided with a complementary trapezoidal shape, to provide a gradual increase in lateral flexibility in the sheet in the direction of the terminal end of the sheet 250. In one embodiment, the apertures 272 are provided in a nitinol sheet having a thickness of about 0.0020 inches, an axial length of about 51 mm and a width of about 6.0 mm. The length of the terminal end 254 is approximately 5.3 mm. The sheet is provided with 4 supports 270 apart from the edges of the sheet. Each support has a width of about 1.24 mm at the first end 274 and about 0.7 mm at the second end 276.

In another design, holes of a given diameter are spaced more closely together near the edge of the sheet thus allowing more holes per row and removing more metal per row to reduce spring force. Other designs may include holes of any shape, cone-shaped slots, serrated ends, tapered ends, changes in metal thickness through etching, drawing, rolling or other means known to those skilled in the art which would result in spring force reduction at the critical terminal ends, as defined above.

Thus, the benefits of the present invention can be accomplished through any of a variety of structures which provide a gradual increase in flexibility towards the axial ends of the sheet. In general, the sheet may be considered to be divided into a central zone, having a first terminal end on a first end thereof and a second terminal end on a second end thereof. In many embodiments, the central zone will have a relatively constant flexibility or spring force characteristics throughout its axial length. Each of the terminal ends will have a relatively increasing degree of flexibility throughout their axial lengths, to permit the axial ends of the sheet to conform to a portion of either the inside or outside surface of the cylindrical configuration assumed by the sheet when implanted in a vessel.

Although the present invention has been described in terms of certain preferred embodiments, variations of the invention will become apparent to those of skill in the art in view of the disclosure herein. Accordingly, the scope of the invention is intended to be limited solely by the attached claims, and not by specific structural recitations contained herein.

What is claimed is:

1. A radioactive tubular prosthesis, comprising:
   a flexible sheet having a first edge and a second edge, the sheet rollable into a tube such that the first edge is disposed on the inside of the tube and the second edge is disposed on the outside of the tube;
   a first transition zone near the first edge; and
   a second transition zone near the second edge;
   wherein the first transition zone has an increasing flexibility in the direction of the first edge, and the second transition zone has an increasing flexibility in the direction of the second edge, wherein the increased flexibility is achieved by having increasingly less sheet material in the first and second transition zones in the direction of the first and second edges respectively, and at least a portion of the sheet has a radioactive coating.

2. A tubular prosthesis as in claim 1, wherein the sheet further comprises an intermediate zone of relatively constant flexibility between the first and second transition zones.

3. A tubular prosthesis as in claim 2, wherein the first transition zone has an axial length of no more than about 20% of the axial length of the sheet.

4. A tubular prosthesis as in claim 1, wherein the first transition zone comprises a series of apertures, said apertures becoming prooressively larger in the direction of the first edge.

5. A tubular prosthesis as in claim 1, wherein the first transition zone comprises a series of apertures, said apertures becoming more numerous in the direction of the first edge.

6. A tubular prosthesis as in claim 1, wherein the first transition zone comprises a series of trapezoidal apertures ninning axially along the length of the first transition zone, said trapezoidal apertures having their shorter parallel side pointing away from the first edge.

7. A tubular prosthesis as in claim 2, wherein the first transition zone is thinnest at the first edge, becoming progressively thicker in the direction of the intermediate zone.

8. A tubular prosthesis as in claim 5, wherein the apertures are sized within the range of from about 2 to 10 microns.

9. A self expandable radioactive tubular prosthesis having a plurality of ports through the side wall thereof, the prosthesis comprising a flexible sheet having a plurality of perforations therein rolled a first number of revolutions about an axis into a first, insertion diameter, the prosthesis radially expandable under its own bias by unrolling to a substantially cylindrical prosthesis having second, implanted diameter having a second, smaller number of revolutions, wherein some of the perforations are inclined at an anile with respect to the axis which is different from the inclination of other of the perforations with respect to the axis, and a sufficient number of perforations through adjacent layers of the sheet align to produce a plurality of ports extending all the way through the side wall of the prosthesis, the sheet provided with zones of differing spring strength so that an inner most revolution of the sheet conforms substantially to the cylinder, and at least a portion of the sheet has a coating comprising at least one radioisotope.

10. A tubular prosthesis, comprising:
   a flexible sheet, having a longitudinal axis and at least first, second, and third groups of apertures extending therethrough;
   the first group comprising a first plurality of parallel slots inclined at a first angle with respect to the longitudinal axis;
   the second group comprising a second plurality of parallel slots inclined at a second angle with respect to the longitudinal axis;
   the first, second, and third groups of apertures arranged on the sheet such that when the sheet is wrapped about an axis through at least about three revolutions to form a tubular prosthesis, apertures from the first, second, and third groups align to produce a plurality of ports extending through the side wall of the prosthesis; and
   a radioactive coating on at least a portion of the sheet comprising at least one radioisotope.

11. A radioactive intraluminal stent implantable in a body vessel lumen, comprising:

a tubular body having a side wall and an inner lumen with an axial length extending between first and second ends of the tubular body, said tubular body formed of a sheet of bio-compatible material forming said side wall and inner lumen when placed in the vessel lumen in an expanded roll state, said sheet having a sheet length providing said first and second overlapping layers when said sheet is in the expanded roll state and a sheet width corresponding to said axial length; and first and second perforation zones formed in first and second portions of said sheet displaced from one another along said sheet length, said first perforation zone having a first plurality of elongated perforations extending in parallel with one another in a first direction, and said second perforation zone having a second plurality of elongated perforations extending in parallel with one another in a second direction differing from said first direction; and at least one transition zone on the sheet having a different spring force than at least one other portion of the sheet, transition zone exposed to the inner lumen; and a radioactive coating on at least a portion of said sheet, wherein the first and second perforation zones substantially overlap one another when said sheet is rolled up into said tubular body having at least two layers in the vessel lumen and provide openings in said side wall through aligned portions of said elongated perforations.

* * * * *

UNITED STATES PATENT AND TRADEMARK OFFICE
CERTIFICATE OF CORRECTION

PATENT NO.      : 6,261,320 B1
DATED           : July 17, 2001
INVENTOR(S)     : Lisa A. Tam and Brett A. Trauthen It is certified that error appears in the above-identified patent and that said Letters Patent is hereby corrected as shown below:

<u>Column 36,</u>
Line 14, please delete "prooressively" and insert therefore, -- progressively --;
Line 22, please delete "ninning" and insert therefore, -- running --

Signed and Sealed this

Sixth Day of May, 2003

JAMES E. ROGAN
*Director of the United States Patent and Trademark Office*